United States Patent
Redzovic et al.

(10) Patent No.: US 12,390,324 B2
(45) Date of Patent: *Aug. 19, 2025

(54) POSTERIOR CHAMBER PHAKIC INTRAOCULAR LENS

(71) Applicant: PHYSIOL, Angleur (BE)

(72) Inventors: Suad Redzovic, Jupille sur Meuse (BE); Renzo Bucca Puy, Liege (BE)

(73) Assignee: PHYSIOL, Angleur (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/760,376

(22) Filed: Jul. 1, 2024

(65) Prior Publication Data
US 2024/0350253 A1   Oct. 24, 2024

Related U.S. Application Data

(63) Continuation of application No. 17/501,052, filed on Oct. 14, 2021, now Pat. No. 12,023,238.

(51) Int. Cl.
*A61F 2/16* (2006.01)

(52) U.S. Cl.
CPC ............ *A61F 2/1602* (2013.01); *A61F 2/161* (2015.04); *A61F 2/1664* (2013.01); *A61F 2002/1681* (2013.01); *A61F 2002/1689* (2013.01)

(58) Field of Classification Search
CPC .......... A61F 2/161; A61F 2/16; A61F 2/1613; A61F 2/1602; A61F 2/1601; A61F 2/1164; A61F 2002/1681; A61F 2002/1689
See application file for complete search history.

(56) References Cited

U.S. PATENT DOCUMENTS

| 4,298,994 | A |   | 11/1981 | Clayman |
|---|---|---|---|---|
| 4,547,914 | A |   | 10/1985 | Castleman |
| 4,575,878 | A | * | 3/1986 | Dubroff ............... A61F 2/16 623/6.53 |
| 4,673,539 | A |   | 6/1987 | Hammar et al. |
| 4,685,920 | A |   | 8/1987 | Fritch |
| 4,704,125 | A | * | 11/1987 | Ruminson ............ A61F 2/16 623/6.45 |
| 4,759,763 | A | * | 7/1988 | Bissonette ......... A61F 2/1613 623/6.21 |
| 4,990,159 | A | * | 2/1991 | Kraff .................. A61F 2/1613 623/6.49 |

(Continued)

FOREIGN PATENT DOCUMENTS

| EP | 0934038 B1 | 8/1999 | |
| WO | WO-9712564 A1 * | 4/1997 | ............ A61F 2/1629 |

(Continued)

*Primary Examiner* — Seema Mathew
(74) *Attorney, Agent, or Firm* — Morgan, Lewis & Bockius LLP

(57) ABSTRACT

The present invention relates to a posterior chamber phakic intraocular lens (1) comprising a central optical part (2), a peripheral haptic part (3) having distal support elements (4) arranged for supporting the intraocular lens (1) on a ciliary zonule, elongated flexible footplates (5) mounted on the support elements (4), each having a distal lateral border (53) arranged for stabilizing the intraocular lens (1) into a ciliary body (98), and manipulation pockets (6) on a surface of the support elements (4), each being associated with one of the elongated flexible footplates (5).

20 Claims, 10 Drawing Sheets

(56) References Cited

U.S. PATENT DOCUMENTS

| | | | |
|---|---|---|---|
| 5,047,051 A * | 9/1991 | Cumming | A61F 2/16 623/6.45 |
| 5,201,763 A * | 4/1993 | Brady | A61F 2/1664 623/6.11 |
| 5,258,025 A | 11/1993 | Fedorov et al. | |
| 5,919,230 A * | 7/1999 | Sambursky | A61F 2/1616 623/6.44 |
| 6,425,917 B1 * | 7/2002 | Blake | A61F 2/1602 623/6.47 |
| 6,749,633 B1 | 6/2004 | Lorenzo et al. | |
| 7,097,660 B2 * | 8/2006 | Portney | A61F 2/1602 623/6.37 |
| 7,455,691 B2 * | 11/2008 | Feingold | A61F 2/1602 623/6.49 |
| 8,523,942 B2 * | 9/2013 | Cumming | A61F 2/1616 623/6.37 |
| 10,973,624 B1 * | 4/2021 | Clarke | A61F 2/16 |
| 11,284,992 B2 * | 3/2022 | Collins | A61F 2/0077 |
| 12,023,238 B2 * | 7/2024 | Redzovic | A61F 2/161 |
| 2001/0044657 A1 * | 11/2001 | Kellan | A61F 2/1602 623/6.43 |
| 2002/0004682 A1 * | 1/2002 | Zhou | A61F 2/1602 623/6.36 |
| 2002/0116062 A1 * | 8/2002 | Portney | A61F 2/1602 623/6.46 |
| 2003/0097177 A1 * | 5/2003 | Tran | A61F 2/1601 623/6.47 |
| 2004/0243232 A1 * | 12/2004 | Cumming | A61F 2/1613 623/6.37 |
| 2005/0021140 A1 | 1/2005 | Liao | |
| 2005/0096741 A1 | 5/2005 | Cumming | |
| 2005/0149184 A1 * | 7/2005 | Bogaert | A61F 2/1602 623/6.14 |
| 2006/0095127 A1 * | 5/2006 | Feingold | A61F 2/1601 623/6.14 |
| 2006/0100704 A1 | 5/2006 | Blake et al. | |
| 2006/0259140 A1 | 11/2006 | Dell | |
| 2007/0168028 A1 | 7/2007 | Tran et al. | |
| 2007/0239274 A1 * | 10/2007 | Kellan | A61F 2/1602 623/6.51 |
| 2007/0244560 A1 | 10/2007 | Ossipov et al. | |
| 2008/0109078 A1 | 5/2008 | Rozakis et al. | |
| 2008/0294254 A1 * | 11/2008 | Cumming | B29D 11/023 623/6.37 |
| 2010/0131061 A1 * | 5/2010 | Callahan | A61F 2/1613 623/6.49 |
| 2012/0310342 A1 | 12/2012 | Nguyen et al. | |
| 2012/0323320 A1 * | 12/2012 | Simonov | A61F 2/1624 623/6.22 |
| 2012/0330415 A1 * | 12/2012 | Callahan | A61F 2/1694 623/6.43 |
| 2014/0330375 A1 * | 11/2014 | McCafferty | A61F 2/1635 623/6.34 |
| 2016/0095699 A1 | 4/2016 | Zaldivar | |
| 2016/0143727 A1 * | 5/2016 | Liao | A61F 2/15 264/2.6 |
| 2016/0346076 A1 * | 12/2016 | Paul | A61F 2/161 |
| 2018/0143455 A1 * | 5/2018 | Chin | A61F 2/16 |
| 2018/0161153 A1 | 6/2018 | Kahook et al. | |
| 2018/0280133 A1 * | 10/2018 | Sri | A61F 2/15 |
| 2019/0000610 A1 * | 1/2019 | Willis | A61F 9/007 |
| 2019/0076241 A1 * | 3/2019 | Alarcon Heredia | A61F 2/1624 |
| 2019/0183635 A1 * | 6/2019 | Macinnis | A61F 2/1613 |
| 2021/0161652 A1 | 6/2021 | Barnett | |
| 2021/0307898 A1 * | 10/2021 | Ben Nun | A61F 2/1629 |
| 2021/0361411 A1 * | 11/2021 | Pagnoulle | A61F 2/161 |
| 2022/0000605 A1 * | 1/2022 | Clarke | A61F 2/1694 |
| 2023/0020167 A1 * | 1/2023 | Cable, II | A61F 2/147 |
| 2023/0123616 A1 * | 4/2023 | Redzovic | A61F 2/161 623/6.43 |

FOREIGN PATENT DOCUMENTS

| | | | |
|---|---|---|---|
| WO | 98/17205 A1 | 4/1998 | |
| WO | 01/34066 A1 | 5/2001 | |
| WO | WO-0187189 A2 * | 11/2001 | A61F 2/1602 |
| WO | 2008/051850 A2 | 5/2008 | |
| WO | 2014/108100 A1 | 7/2014 | |
| WO | WO-2014167425 A1 * | 10/2014 | A61F 2/16 |
| WO | WO-2015026226 A1 * | 2/2015 | A61F 2/1648 |
| WO | WO-2015103116 A2 * | 7/2015 | A61F 2/16 |
| WO | 2016/054624 A1 | 4/2016 | |
| WO | 2016/191614 A1 | 12/2016 | |
| WO | 2020/035534 A1 | 2/2020 | |
| WO | 2020/239892 A1 | 12/2020 | |

* cited by examiner

POSTERIOR CHAMBER PHAKIC INTRAOCULAR LENS

RELATED APPLICATIONS

The application is a continuation application of U.S. patent application Ser. No. 17/501,052, filed Oct. 14, 2021, which is incorporated by reference herein in its entirety.

TECHNICAL FIELD

The invention concerns an intraocular lens (IOL). More specifically, it concerns a posterior chamber phakic IOL.

PRIOR ART

Generally speaking, phakic IOLs are IOLs intended to be placed in an eye in order to correct defects of vision. These IOLs are generally implanted in patients who are still young, as a complement to the natural crystalline lens.

Posterior chamber phakic IOLs are phakic IOLs that are intended to be implanted in an area of the eye between a posterior surface of the iris and an anterior surface of the lens, and supported around the ciliary body of the eye.

A limit in implantation of such an IOL lies in the fact that it is likely to be positioned differently from one eye to the other on the basis of parameters, especially the anatomy of the posterior chamber, the size of which usually varies by several millimeters from one patient to another. In particular, implantation of a posterior chamber phakic IOL, the size of which may not be adapted, would risk leading to more of less serious medical complications for the patient, such as:
  for example, in a case where the phakic IOL is too small with respect to the size of an available posterior chamber anatomical space for IOL implantation: a contact of the IOL with the crystalline lens that generates a cataract of the eye, or a loss in the corrective power of the phakic IOL, or that has an impact on vision precision;
  or for example, in a case where the phakic IOL is too large with respect to the size of this anatomical space: a pupillary block, a glaucoma, an inflammation, an iris depigmentation, or a depression between the anterior and posterior chambers of the eye after a pupillary block.

Production and use of various sizes of phakic IOLs on the basis of general eyes anatomy cannot fully overcome this defect. Indeed, shortcomings in terms of the stability of the position of such a phakic IOL once it is implanted in an eye are likely to lead to the same medical complications.

As an attempt to solve this problem, document WO 2020/035534 A1 discloses a posterior chamber phakic IOL comprising a double haptic structure made of a peripheral haptic part comprising support elements arranged to lie on the ciliary zonule and elongated haptics having a proximal extremity mounted on a proximal portion of the peripheral haptic part and a free distal extremity to hook the IOL into the eye ciliary sulcus. These haptics allow to compensate the size variations of said anatomical space, so that the double haptic structure globally allows stabilization of the IOL position in the eye.

The elongated haptics of this IOL are nevertheless difficult to see and to maneuver during the implantation process in the eye. It this then desirable to provide a posterior chamber phakic IOL easier to implant, but sufficiently stable in implantation position.

DISCLOSURE OF THE INVENTION

An object of the present invention is to provide a posterior chamber phakic IOL both adapted to a wide class of eye anatomy and easy to implant in an eye.

For this purpose, the invention provides a posterior chamber phakic IOL comprising:
  an anterior surface and a posterior surface;
  a central optical part comprising a lens, and
    extending radially relative to an optical axis directed from the anterior surface to the posterior surface;
  a peripheral haptic part
    circumferentially mounted on the central optical part,
    extending radially outward and posteriorly relative to the central optical part, and comprising distal support elements arranged for supporting the IOL on a ciliary zonule when the IOL is in an implantation position in an eye;
  at least one elongated flexible footplate
    extending radially beyond the peripheral haptic part, and comprising a first extremity mounted on the peripheral haptic part;
  wherein the elongated flexible footplate comprises:
    a second extremity mounted on one of the support elements; and
    a distal lateral border extending circumferentially and radially outward relative to the central optical part, and arranged for stabilizing the IOL into a ciliary body when the IOL is in the implantation position in the eye.

Said one of the support elements preferably comprises a manipulation pocket on the IOL anterior surface, at least partially radially aligned with the elongated flexible footplate, and dimensioned for cooperating with a tip of a manipulation tool by a (keyed) engagement of the tip into the pocket, so that a moving of the elongated flexible footplate can be induced by a moving of the tool.

This IOL allows to reach a good compromise between the necessity of improving the IOL stability in implantation position, and to implant it easily. As the IOL of document WO 2020/035534 A1, this IOL comprises a central optical part equipped with two distinct and complementary haptic structures: firstly, the peripheral haptic part comprising the distal support elements, and, secondly, the at least one elongated flexible footplate (said "the footplate" hereafter, although the IOL preferably comprises two or four of such elongated flexible footplates). The peripheral haptic part forms, together with the central optical part, a "dome assembly", the feet of which are the support elements arranged distally in order to support the IOL on the ciliary zonule. As the footplate extends radially beyond this dome assembly, it also allows stabilization of the IOL into the ciliary body. The geometry and the flexibility of the footplate fully contributes to this IOL stability in implantation position. In order to make the IOL easier to implant, the footplate is completely mounted by its extremities on the flexible haptic part. Although this reduces slightly the adaptability of the footplate in comparison with a long and freely ended footplate as in document WO 2020/035534 A1, this new geometry of footplate makes it much easier to manipulate during an implantation process. This feature is further enhanced by the preferred presence of the manipulation pocket on the support element on which at least one extremity of the footplate is attached. In particular, the geometry and the flexibility of the footplate still allows to adapt the IOL to a wide class of eye anatomies, but the manipulation difficulty that this could generate is fully compensated by the attachment of the footplate extremities to the peripheral haptic part, and by the advantageous presence and position of the pocket.

The above-mentioned technical effects are now commented in detail. In particular, as it is explained below, the IOL is particularly stable axially (i.e. in parallel to the optical axis), radially (i.e. in perpendicular directions with respect to the optical axis) and circumferentially (i.e. in rotations around the optical axis) in its implantation position.

The peripheral haptic part allows stabilization of the IOL in parallel to the optical axis. The support elements are arranged at the distal extremities of the peripheral haptic part and designed for supporting the IOL dome assembly on the ciliary zonule. The dome assembly is configured to be anteriorly above the eye's natural crystalline lens so that it encloses the lens at least anteriorly. As a consequence, the distance, called "the vault", measured along the optical axis between the crystalline lens anterior surface and the IOL posterior surface, is defined and stabilized. It can be assimilated to a safety distance required in order to avoid a contact or too much proximity between the crystalline lens and the IOL. A safety distance between the IOL and the eye iris is similarly defined and stabilized as being the distance between the IOL anterior surface and the posterior surface of the iris conceived as a virtual iris plan occupying the pupil eye (in rise opening).

The vault is preferentially comprised and/or adjustable between 100 and 1000 µm, more preferably between 300 and 750 µm, with or without radial and/or axial compression. Enough space is then available between the IOL and both the crystalline lens and the iris, which compensates potential anatomical size defects in the eye posterior chamber, or possible positioning defects of the IOL, to sharply reduce the risks of complication for the patient. According to an embodiment of the invention, the vault is titrated by sculpting the IOL posterior surface such that it follows a contour of a natural crystalline lens for which it is intended to be implanted.

The structure of the dome assembly is adapted to a wide range of eye anatomy base on a choice of a posterior surface more curved than the anterior surface of any crystalline lens and on a choice of peripheral haptic part external diameter (measured perpendicularly to the optical axis) compatible with a wide range of eye posterior chamber anatomy. In a more specific way, this diameter is preferably comprised between 9.50 and 11.50 mm, and e.g. of about 9.50, 9.60, 9.70, 9.80, 9.90, 10.00, 10.10, 10.20, 10.30, 10.40, 10.50, 10.60, 10.70, 10.80, 10.90, 11.00 or 11.10 mm. Three diameter values of 9.50, 10.40 and 11.10 mm are advantageously sufficient to cover any posterior chamber anatomy as it will be explained hereafter. The posterior surface of the dome assembly is preferably smooth and (posteriorly) concave. It has a radius of curvature more preferably comprised between 8 and 11 mm, again more preferably between 9 and 10 mm included. The radius of curvature is preferably chosen as the smallest average radius of curvature of an anterior surface of a crystalline lens, typically 9.0, 9.1, 9.2, 9.3, 9.4, 9.5, 9.6, 9.7, 9.8, 9.9 or 10.0 mm. It is also noted that this radius of curvature is well defined given that the dome assembly posterior surface is smooth and then (mathematically) regular. In particular, the posterior surface at the junction between the central optical and the peripheral haptic parts preferably does not comprise irregularity or angular points.

The dome assembly then tops the crystalline lens when the IOL is in an implantation position in the eye (namely, when the IOL is in a normal use in the eye), resting on the ciliary zonule, and stabilizing the IOL in parallel to the optical axis. The footplate, for its part, extends radially substantially beyond the dome assembly in the eye posterior chamber, for laying into the ciliary body. The flexibility and the geometry of the footplate allow the IOL to adapt itself to internal size variations of the posterior chamber anatomical space available for the IOL (known as a being a "ciliary body-to-ciliary body" measurement, being preferably a ciliary body-to-ciliary body distance taking into account a elasticity penetration factor of the footplate into the eye ciliary body), across a range of internal eye dimensions including those which cannot be accurately estimated pre-operatively. While the dome assembly external diameter is substantially constant in IOL implantation position, the IOL global external diameter can then vary due to the flexibility of the footplate, adapting then to the eye posterior chamber anatomy. Advantageously, the use of a single IOL model according to the invention is then enough for a broad range of patient eye anatomies.

The footplate also enables the stabilization of the IOL in rotation in a plane perpendicular to the optical axis so that the variation in this anatomical space (acknowledged to be greater in one orientation than another because of its "oval" shape) can be fully compensated. This footplate is circumferentially and radially extended such that its distal lateral border is adjusted to lay and/or hook and/or stabilize itself into the ciliary body, playing a role of circumferential anchors for the IOL.

This feature is important in the embodiment for which the IOL is a toric implant comprising a optic with a cylinder to correct astigmatism. In this case, the stability of the angular position of the IOL lens in the perpendicular plane, called "rotational stability", is crucial in order to guarantee the expected IOL optical results. In this case, the footplate allows to maintain the IOL lens in a central optical zone and then to avoid possible decentering of the IOL with respect to the eye optical axis which could affect the IOL optical results.

The first and second extremities of the footplate are mounted on the peripheral haptic part which improves the maneuverability of the footplate during the IOL implantation process. In addition, at least the first extremity is mounted more specifically on one of the support element, in other word, the most distally on the peripheral haptic part, so that the footplate length is reduced for reaching the ciliary body. Advantageously, such reduced footplate length means a more maneuverable footplate during the IOL implantation process, so that the IOL is easier to implant. These distinguishing innovative features allow to compensate the elongated geometry and the flexibility of the footplate, which are important for the above mentioned IOL stabilization purpose. In fact, the footplate is long, thin and clear, and then difficult to see and to maneuver under the eye iris. It could flip easily if it was too long and/or with a free extremity. Advantageously, the footplate of the present invention overcomes these difficulties.

As first and second extremities of the footplate are mounted on the peripheral haptic part, the footplate extends globally along a partial loop, radially outward with respect to the optical axis from the second extremity, then radially inward with respect to the optical axis to the first extremity, reaching so a distal extremity of the loop, at the IOL external diameter. The distal lateral border has then a form of a portion of this partial loop arranged distally to stabilize the IOL into the ciliary body. The distal lateral border advantageously proposes then a potentially wide contact surface with the ciliary body.

It is quite important to have a easily implantable IOL due to the tricky implantation position between the eye natural crystalline lens and the iris. Fewer manipulations needed to position the IOL allow to avoid error that could negatively impact the patient. For further improving the footplate maneuverability during the implantation process, the support element on which is mounted the second extremity of the footplate is preferably also endowed with the above-mentioned manipulation pocket. The invention is nevertheless not necessarily limited to the presence of the pocket, although it is preferable, as the features of the footplate discussed above already allow to distinguish advantageously the IOL according to the invention from the prior art.

This pocket is arranged close to the footplate, in particularly at least partially radially aligned with it. As at least the second extremity of the footplate is attached to the same support element, it is possible to modify the footplate position by moving the tip of the tool in an appropriate way in the pocket. No direct manipulation of the footplate is needed which strongly reduce the risk of manipulation error. Indeed, as the footplate is thin and clear, it is easy to miss out, to pass through the IOL posterior surface and to touch sensible intraocular tissues, e.g. the crystalline lens. By circumscribing the tip movement in such a pocket at level of the IOL anterior surface, no such handling error can occur.

This pocket is also advantageous when the IOL has to be manipulate under the eye iris which is opaque. Indeed, it allows to guide the tip of the tool on the anterior surface by a keyed engagement of the tip into the pocket. So, it is not necessary for the surgeon to see the footplate under the iris (which is in general very difficult) for positioning it correctly. It is advantageously enough for the surgeon to perform appropriate (known) movements with the tool, when the tip is engaged in the pocket, for positioning the footplate under the iris, without necessarily seeing it. Preferably, the pocket is especially dimensioned for fitting with these movements and guiding the surgeon during the implantation process.

In the framework of the present document, an "optical axis" of an eye consists preferentially in a vector crossing the eye from one side to the other, directed by its "anterior segment", comprising successively, the cornea, the iris and the lens, to its "posterior segment", comprising the retina. For a phakic IOL according to the invention in an implantation position in an eye, the optical axis of the eye is directed from the IOL anterior surface to the IOL posterior surface and preferably corresponds to the optical axis defined intrinsically with respect to the IOL. In particular, the term "optical axis" is preferably used in the present document as the reference axis with respect to the eye and/or to the IOL.

In the framework of this document, an "anterior" (or resp. "posterior") side and/or surface of an eye or IOL part or consists preferably in a side and/or surface located upstream (or resp. downstream) of said part with respect to the vector defined by the optical axis. This definition extends naturally to the term "anteriorly" (or resp. "posteriorly"). By the way of examples, in an eye, the iris is located anteriorly with respect to the crystalline lens; a posterior surface of the iris is then a part of the iris that is the closest to the crystalline lens.

Likewise, such side and/or surface is said "anteriorly concave" (resp. "anteriorly convex") when it is seen as concave (resp. convex) by looking at the optical surface in the same direction and the same sense as the vector defined by the optical axis (i.e. following light rays propagations). It is said "posteriorly concave" (resp. "posteriorly convex") when it is seen as concave (resp. convex) by looking at the optical surface in the same direction and the opposite sense as the vector defined by the optical axis. In this document, the term "concave" is generally used as corresponding to "posteriorly concave" when the context of its use make it clear for the skilled person that this is its meaning.

The aforementioned notions of anteriority, posteriority or even of an optical axis relative to parts of an eye and/or of an IOL are well known to person skilled in the art. In particular, the IOL according to the invention is configured to be positioned in the posterior chamber of an eye, so that its anterior surface is at least partially facing the iris of the eye and so that its posterior surface is at least partially facing the crystalline lens of the eye.

In the framework of this document, the term "axial" and "axially" refer to directions in parallel to the optical axis. It is preferably said that part of an IOL extends:
  "radially" if it extends according to vectors perpendicular to the optical axis,
  "radially outward" if the vectors are directed from a point in common with the optical axis to points of a circle centered at this common point; and
  "radially inward" if the vectors are directed in the opposite sense.

It is also preferably said that a part of an IOL extends "circumferentially" when it extends preferably according to a circular arc on a plane perpendicular to the optical axis centered on an intersection point of this plane and the optical axis. These notions of radial and circumferential extensions refer to known systems of polar coordinates in each plane perpendicular to the optical axis.

It is well known by a person skilled in the art that the adjective "distal" refers to a part of a portion of a body the furthest form a reference organ or from a trunk of a body, and that the adjective "proximal" refers to a portion of a part of a body the closest to a reference organ or to a trunk of a body. In the framework of this document, these definitions also apply to parts of an eye and/or of an IOL, relative to a distance with respect to the referential optical axis. By the way of examples, preferably, a proximal portion of an IOL according to the invention may comprise the central optical part and/or a part of the IOL around a central part, and a distal portion of an IOL according to the invention may comprise the footplate, or at least its distal lateral border.

In particular, the term "distal" concerning the "distal lateral border" of the footplate refers preferentially to the set of points of the footplate each being the furthest from the optical axis along a radius perpendicular to the optical axis.

In the framework of the present document, the use of the indefinite article "a", "an" or the definite article "the" to introduce an element does not exclude the presence of a plurality of these elements. Likewise, the terms "first", "second", "third" and "fourth" are solely used to differentiate elements and do not imply any order in these elements.

In the framework of this document, the use of the verbs "comprise", "include" or any other variant, as well as their conjugational forms, cannot in any way exclude the presence of elements other than those mentioned.

The IOL and, specifically, the peripheral haptic part and the footplate are preferably made of a biocompatible, flexible and highly resistant material. This material is preferably a hydrophilic material.

The global thickness in this material varies radially for providing more or less flexibility to parts of the IOL. In the framework of the present document, the "thickness" is measured in parallel to the optical axis. It is preferably greater for the peripheral haptic part than for the footplate.

Indeed, these two haptic structure constitutes a compromise between on one hand, the need for stability and compliance with intraocular structures, and on the other hand, the need for rigidity, avoiding excessive exertion of force and trauma to delicate intraocular structures, many of which are complex and not visible during or prior to implantation. They are structured to ensure that the vault as described above is not significantly affected from a compression of the IOL exerted on its edge by the eye internal anatomy. In particular, the dome assembly has a "rigid" structure, induced by a greater thickness in material in average than that of the footplate, and/or by a flared and/or wide and/or thick shape of the support elements. The rigidity and geometric features of the dome assembly is adapted to a wide range of eye anatomy. In contrast, the "flexible" characteristic of the footplate is preferably induced by the nature of this material combined with its elongated geometry and its low average thickness, in particular in comparison with that of the dome assembly.

More specifically, according to a preferred embodiment of the IOL of the invention, the thickness of the peripheral haptic part radially decreases from the central optical part to the pocket. It is preferably at least 50%, and preferably again twice, larger on average than the footplate thickness. This averaging can simply be considered as a regular discrete or integral averaging of the thickness over a plane perpendicular to the optical axis.

By the way of examples, the peripheral haptic part radially decreases from between 0.70 and 0.50 mm, preferably about 0.60 mm, at its border with the central optical part, to between 0.25 and 0.15 mm, preferably about 0.18 mm, at the level of the proximal border of the pocket (but not inside the pocket).

The footplate has, for its part, a preferably constant thickness along all its extension, e.g. of about between 0.10 and 0.20 mm, preferably of about 0.15 mm, contributing to its great flexibility as discussed above.

Preferably, the thickness of the peripheral haptic part is specifically targeted to allow the IOL to reside at a determined distance from the anterior surface of the crystalline lens by virtue of selectively titrating the curvature of the IOL anterior and/or the posterior surfaces such that the posterior surface mimics the (anterior) curvature of the crystalline lens.

The radii of curvature of the IOL anterior and posterior surfaces are also optimized regarding the targeted dioptric power, and in a such way that the central thickness of the central optical part is kept substantially constant across a whole diopter range. This is preferably comprised between 0.20 and 0.40 mm. For instance, it is about 0.20 mm for a lens dioptric power comprised between −5 and −20 D, it is about 0.40 mm for and it varies from 0.40 to 0.20 mm for lens dioptric powers respectively varying from −0.5 to −5 D. The central optical surface is preferably substantially anteriorly convex and/or substantially planar and/or perpendicular to the optical axis. This allows to deliver advantageously a vault without the need for compression and therefore flexing of IOL anteriorly.

The term "the footplate" generally refers, in the present document, to the at least elongated flexible footplate. However, the IOL preferably comprises additional footplate(s). Preferably, characterizations provided in the present text for "the footplate" also apply for the other footplates.

The IOL according to the invention preferably comprises either two or four distal support elements and either two or four elongated flexible footplates, preferably at least partially symmetrically arranged, for ensuring a good stability of the IOL under axial and/or radial compressions, as well as in rotation. These numbers of support elements and elongated flexible footplates are nevertheless not limitative of the scope of the invention. For instance, the IOL can comprise a single elongated flexible footplate alone or in combination with any other haptic structure known by a man skilled in the art, e.g. an elongated haptic with a free distal extremity as disclosed in WO 2020/035534 A1. The use of four elongated flexible footplates symmetrically arranged (e.g. on the corners of a rectangle) is preferred because this mitigates any possible tilting effect.

Each elongated flexible footplate of the IOL is preferably associated to a specific manipulation pocket as claimed and described above, so that the number of pockets corresponds preferably to the number of elongated flexible footplates. One pocket can however be used for moving two or more elongated flexible footplates. Such a pocket can extend on one or more support elements e.g. via a proximal portion of the peripheral haptic part, so that the two or more elongated flexible footplates are not necessarily mounted on the same support elements. A support element can also comprise several pockets, each proximal to an extremity of a different elongated flexible footplate. The first extremity of the footplate, as its part, can be mounted on the same support element as the second extremity, on another support element, as well as on a proximal portion of the peripheral haptic part, e.g. between two adjacent support elements. More generally, it will be understood by the skilled person that various configurations of IOL can be considered in the framework of this invention with regard to the number and/or positioning of the support elements, elongated flexible footplates and manipulation pockets. Some preferred of them will be introduced hereafter.

The "elongated" feature of the footplate refers to its thin geometry, which contributes to its flexibility as described above. In particular, the footplate has preferably three dimensions among which its length along a main trajectory of extension, its thickness, and a width measured orthogonally to the two other dimensions. This "elongated" feature can be translated by a length greater than the (average) thickness and the (average) width of the footplate, namely at least twice greater, preferably at least three times greater, and more preferably, more than five times greater. This provides to the footplate a great ability to deform under axial and/or radial compression of the IOL. In comparison to standardly commercialized posterior chamber phakic IOLs having reduced massive distal footplates, the present IOL footplate allows for more flexibility and stability, and then adaptability to a class of eye anatomies estimated more than 50% broader (as it will be commented in view of FIG. 9 hereafter introduced). Although the gain in adaptability is slightly lower than that of the IOL disclosed in the document WO 2020/035534 A1, it is advantageously obtained without major implantation difficulty as it is discussed above. In particular, the IOL according to the invention constitutes then a very good compromise between obtaining a phakic IOL with such improved adaptability and stability, and obtaining a phakic IOL which is easy to implant.

As the two extremities of the footplate are mounted on the peripheral haptic part, the footplate preferably borders a cavity extending from the anterior to the posterior surfaces. This cavity is typically an open cavity. It is generally completely bordered by the footplate and the peripheral haptic part, preferably by the footplate and said one of the support elements.

The term "cavity" is here used as an equivalent to a space empty of the material constituting the IOL. This term is more convenient than "hole" as the cavity is preferably not a hole provided in said material but simply a feature arising from the footplate geometrical features. An IOL production method by providing large holes in said material for defining the footplate can however not be excluded from the scope of the invention.

The above-mentioned cavity has preferably a maximal radial length greater, more preferably at least twice greater, than a maximal diameter of a cross section of the footplate (considered along its main extension trajectory). In other words, the cavity radial length is larger than the width and the thickness of the footplate, so that the footplate thin and elongated geometry is adapted to reach dynamically and flexibly the eye ciliary body. In particular, the flexible haptic is such that, when (strong) radial compression forces occur on the IOL, the haptic is able to deform in such a way that the cavity partially collapse on itself. In other words, in this case, said maximal radial length preferably is divided by two, three, or more.

The footplate may optionally comprise a material fold and/or a lateral recess, e.g. at its extremities, arranged to facilitate and/or to direct the footplate curvature and/or orientation when axial and/or radial pressure is exerted on the IOL. In particular, such material fold and/or lateral recess can play the role of a failsafe mechanism arranged to prevent an excessive force transmission from the footplate to the central optical part. It allows to control such force applied by the footplate to provide a adapted fixation into the ciliary body and to prevent an erosion of delicate intraocular tissues.

The distal lateral border of the footplate optionally comprises smooth ripples arranged to smoothly hook into the eye ciliary body. Advantageously, the ripples facilitate the stabilization of the IOL into a ciliary body when it is in the implantation position in the eye. The ripples give a role of a pin to the distal lateral border to lay and stabilize easier into a ciliary body. These ripples are preferably polished so that their contours cannot irritate the ciliary body or other part of the eye anatomy.

According to a preferred embodiment of the invention, the IOL has a smooth lateral chamfer extending smoothly and continuously, from said support element on which is mounted the footplate second extremity, to a first portion of the distal lateral border. This chamfer extends on the support element and on the first portion of the distal lateral border, providing a continuous and smooth lateral transition between the peripheral haptic part and the footplate via one of the footplate extremity, e.g. the second extremity. This transition is particularly helpful for implanting the IOL because it allows to insert smoothly the footplate under the eye iris preferably by use of the manipulation pocket. In particular, the existence of such chamfer also implies that said one of the footplate extremity is mounted laterally on a side of the support element, in such a way that the distal lateral border continues smoothly this side of the support element.

Preferably, the smooth lateral chamfer also extends proximal to the support element, laterally, on all or part of the peripheral haptic part. Preferably, the whole chamfer extends orthogonally to the optical axis, and extends further circumferentially on the distal lateral border, following the above discussed loop shape of the latter.

The whole lateral chamfer has then a smooth external surface which is more preferably (posteriorly) concave. It is typically anteriorly oriented. As it is concave, the external surface does then not comprise curvature turning points, so that the partial loop shape of the distal lateral border turns from a lateral side of the support element to a more centered position on the peripheral haptic part, e.g. converging toward an axis perpendicular to the optical axis, which makes the IOL advantageously easier to manipulate and to implant without injury risk for the intraocular tissues.

In the framework of the present document, the term "first diameter" refers to an IOL external diameter, and the term "second diameter" refers to a peripheral haptic part external diameter, those two diameters being measured perpendicularly to the optical axis. The dome assembly is then constricted to a cylinder of the second diameter, while the footplate extends further radially to the first diameter.

The second diameter is preferably comprised between 9.50 and 11.10 mm, and corresponds to a smaller sized ciliary body (or more precisely a smaller available anatomical space), so that the dome assembly has a size compatible with a broad range of eye anatomies. In particular, the dome assembly is small enough to avoid undergoing itself some compressions when the IOL is in the implantation position.

The first diameter, for its part, is preferably comprised between 12.50 and 14.00 mm, more preferably between 12.70 and 13.60 mm, in particular when no axial and/or radial compression is exerted on the IOL. The footplate extends in particular on a radial length comprised between the difference of the second diameter and the first diameter, corresponding to a haptic flexible contribution that can be contracted to fill the gap between the dome assembly and the ciliary body. The IOL according to the invention is then particularly well adapted to a broad range of eye anatomies with a planned resultant vault that is stable and very low dependent on the axial and/or radial compression of the footplate.

In order to cover all eye anatomies, several IOL sizes can be needed with different first and second diameters. Two or three sizes of IOL are sufficient to cover all eye anatomies, e.g. with first diameters among 12.7, 13.2 and 13.6 mm and second diameters among 9.5, 10.4 and 11.1 mm. Preferably, the latter second diameters are respectively associated with the mentioned first diameters in the same order. This number of IOL sizes is in particular reduced in comparison with known phakic IOLs comprising massive distal footplates given that each of the present IOL is adapted to a broader class of eye anatomies.

According to a preferred embodiment of the invention, at least one, and preferably each, of the distal support elements is elongated along a circular arc with a central angle comprised between 20 and 80°, preferably, between 40 and 70°, more preferably of about 60°. As it is known, the term "central angle" refers to the angle subtended by the circular arc. In particular, it is the angle at a center of circle of the circular arc of a triangle whose vertex are said center and the two extremities of the circular arc.

Advantageously, the support elements as feet of the dome assembly are then wide and circular, providing a stable and rigid base for supporting the IOL on the ciliary zonule when the IOL is in an implantation position in an eye. The circular arc is typically of the second diameter. At least two footplates are preferably mounted symmetrically by their first and second extremities on each support element.

The pocket is now discussed in more detail below. The pocket plays an advantageous role in the present invention as contributing to a simplified IOL implantation. As described above, in order to be able to manipulate the footplate via the engagement of the tool tip into the pocket, the pocket is arranged on the support element on which is mounted the footplate second extremity, and it is at least partially radially aligned with the footplate. In order words, and preferably, the pocket is arranged close to the footplate, in particular, close to the footplate extremities, at their proximal neighborhood, and/or radially aligned between the optical axis and the footplate.

As mentioned above, the footplate first extremity can be mounted on different position on the peripheral haptic part. It is however preferably mounted on the same support element as the second extremity. As explained above, this allows the footplate to extend from and to the most distal part of the peripheral haptic part, then to reduce the footplate length, so to facilitate its manipulation. In addition, the pocket is then proximal to both footplate extremities on the same support element which make it easier again to manipulate the footplate during the IOL implantation process. In this case, the pocket is preferably substantially radially aligned between the first and second extremities, which improve further the footplate manipulation via the engagement of the tool tip into the pocket.

According to an embodiment of the present IOL, the pocket defines or has the form of a circumferential trench on IOL the anterior surface extending in parallel to the footplate and dimensioned for receiving the tip of the tool along the trench. More specifically, the trench is designed and dimensioned in such a way that it is possible to move the IOL with the tool for inserting it under the eye iris. The trench extends circumferentially preferably along a distal border of the support element, from a close proximal neighborhood of the second extremity to a close proximal neighborhood of the first extremity. For instance, the distance between those extremities and the pocket is preferably less than 0.30 mm, and more preferably less than 0.20 mm. The trench design is then perfectly adjusted for receiving the tool tip and moving it appropriately for positioning the footplate thanks this proximity between its extremities and the pocket.

Preferably, the trench is designed similarly to the footplate, and/or it has similar geometric extension features. Preferably, the trench comprises two radially inwards extensions at its two circumferential extremities, in radial mirror symmetries with the footplate extremities. This design of the pocket is adapted in particular for performing appropriate movements with the tool tip allowing to insert the footplate under the iris (as it is illustrated in FIG. 11, that is hereafter introduced).

The trench, or any other form of the pocket, is typically provided in one piece on the IOL anterior surface. In particular, the pocket is not intended to be in communication with the IOL posterior surface. Indeed, the goal is to avoid a passing to the tool tip through the IOL which could hurt intraocular tissues.

According to an embodiment of the IOL pocket fully compatible with the preceding embodiments, it comprises a bottom surface and lateral edges as part of the anterior surface. The bottom surface is preferably rough for increasing the friction and/or hooking of the tool tip into the pocket. The edges are preferably of a height measured axially comprised between 25 and 75%, more preferably of about 50% (+/−5%) of the thickness of the support element on which is mounted the second extremity of the footplate. Such a pocket is in particular easy to manufacture and is fully satisfactory for the above described manipulation purpose. The height of the pocket edges as 50% (+/−5%) of the thickness of the support element is appropriate for having a pocket sufficiently deep for hooking the tool tip and a portion of the support element underlying axially the pocket sufficiently thick for guarantying its resistance.

According to a preferred embodiment of the invention, the footplate distal lateral border extends from said second diameter to the first diameter and has a second portion extending along an arc of circle of the first diameter. The second portion is then in particular composed of the most distal points of the IOL, i.e. the furthest points in absolute radial value. The second portion is preferably not negligible in length. It preferably has a central angle comprised between 5° and 25°, more preferably of about 10° when no axial or radial compression is exerted on the IOL, so that to stabilize strongly the IOL in rotation into the ciliary body. In addition, this central angle can be increased till 45° if the IOL is in its implantation position, i.e. when axial and/or radial compression is exerted on the IOL.

Preferably, the second portion of the distal lateral border is attached to the above-mentioned first portion on which extends a smooth lateral chamfer if the IOL comprises such a chamfer. This attachment is made so that the distal lateral border extends continuously and smoothly along these first and second portions, continuing smoothly laterally the support element on which is mounted the footplate second extremity. This provides the footplate with a smooth design easy to manipulate and to insert under the iris. The distal lateral border consists preferably in these first and second portions. Preferably, the second portion of the distal lateral border is attached to a third portion of the footplate connecting it to the first extremity. This third portion extends preferably (only) radially along a direction having a smaller angle comprised between 5 and 60°, more preferably 7.5 to 40°, e.g. 7.5°, 10°, 15° or 20°, with a (mirror) symmetry axis of the IOL that is perpendicular to the optical axis. This angle allow advantageously to decrease the exerted compression forces on the IOL when it is in its implantation position. In particular, the greater the angle is, the lower are the exerted compression on forces on the IOL. Typically, when such high compression forces occur, the first and third portions flexibly deviated laterally in such a way that the second portion gets significantly closer to the distal border of the corresponding support element, or in other word, in such a way that the corresponding cavity size significantly decreases. For example, the second portion is at least twice, or three time closer to the distal border than when not compression forces is exerted on the IOL.

According to a preferred embodiment of the invention, the footplate extends along a plane whose normal vector forms an angle comprised between −15° and 15° with the optical axis. This angle applies in particular when the IOL is in its implantation position so as to allow an orientation of the footplate that is adequate to lay into the eye ciliary body and to stabilize the IOL. Said normal vector is oriented similarly to the optical axis and the angle sign is preferably considered in a conventional planar trigonometric sense. Preferably, the angle as a value comprised between −5° and −10°, more preferably of about −7°, when the IOL is in production, at least prior to its implantation, so that the insertion of the footplate under the iris is advantageously easier.

According to a hereafter illustrated embodiment of the invention, the IOL comprises two diametrically opposed distal support elements and two pairs of diametrically opposed oriented elongated flexible footplates. The orientation of the footplate is preferably determined by a travel sense along the footplate main extension trajectory, from the second extremity to the first extremity. This symmetrically distributed arrangement of the support elements and elongated flexible footplates provides the IOL with a great stability axially, radially as well as in rotation. In particular, said vault is only partially dependent upon compression lateral forces exerted through the IOL body. When such a compression lateral force occurs, the IOL design absorbs it at least partially, preferably almost totally, within the two pairs of elongated flexible footplates so that the dome assembly is very advantageously more axially stable with few possible axial movements.

The present IOL is preferably shape invariant under rotation of 180° around the optical axis. In other words, the pairs of elongated flexible footplates have an orientation such that there are respectively image one of the other by a rotation of 180° of the IOL around the optical axis. This is advantageous for the case of an IOL lens comprising a curvature irregularity to correct astigmatism, e.g. in the case of a phakic toric IOL. In fact, in this case, it is often necessary to preoperatively rotate the IOL to position it in a proper axis. The design and the rotational symmetry of the elongated flexible footplates facilitate such rotation maneuver during the implantation process.

The phakic intraocular lens is also preferably shape invariant under planar reflections by two orthogonal planes, each comprising the optical axis. This provides the IOL with an advantageous mirror symmetry allowing to avoid twist of the IOL during and after implantation.

Preferably, the closest elongated flexible footplates from two different pairs are spaced by a distance comprised between 5% and 25% of the second diameter. The elongated flexible footplates are also preferably distally oriented in a convergent way toward an axis perpendicular to the optical axis. The distal orientation of each footplate is obtained by natural induction of said orientation on its distal lateral border. In other words, the elongated flexible footplates are globally inwardly oriented and not outwardly oriented from distal corners of the IOL. This makes the elongated flexible footplates easier to insert under the iris during the implantation process as each footplate movement is easier to control.

According to a generally preferred embodiment of the invention, the central optical part comprises a through bore that extends between the anterior surface and the posterior surface of the IOL, and that is arranged to allow a fluid flow between these surfaces when the IOL is in its implantation position. This bore advantageously allows to prevent a second artificial posterior chamber to be induced by the IOL presence, which would undesirably limit a natural liquid flow between spaces anterior and posterior to the IOL. The bore guarantees a full and permanent fluid communication between the eye anterior and posterior chambers. Preferentially, the through bore is located in a center of the central optical part, about its intersection with the optical axis.

Optionally, the IOL also comprises peri-optical holes arranged on the peripheral haptic part, preferably close to its proximal boundary with the central optical part. These peri-optical holes are crossing the anterior surface and the posterior surface of the IOL, and also allow another fluid flow through the IOL, in particular during the implantation process.

According to an embodiment of the IOL, the central optical part has at least an orientation mark on the IOL anterior surface. This orientation mark is in particular useful for orienting the IOL during the implantation process as the central optical part remains mainly visible. This is in particular advantageous for correctly orienting a phakic toric IOL as explained above. The orientation mark can take various forms. Preferably, it consists in aligned small superficial holes on the IOL anterior surface. These holes are obviously not crossing the IOL. The mark can also take the form of at least one superficial line made by laser, mild, or engraving on the anterior surface of the IOL.

The invention advantageously allows a choice of central optical part lens that is best adapted to a defect in vision that is to be corrected in a patient. In particular, according to embodiments of the invention, the central optical part lens consists in a monofocal lens allowing at least one correction from among: a correction of myopia, a correction of hypermetropia, a correction of presbyopia and a correction of corneal astigmatism. According to a particular embodiment of the invention, the lens consists in a refractive or diffractive lens at extended depth of focus, preferably to treat presbyopia. Preferentially, the lens is selected according to the state of the art.

As disclosed above, the IOL according to the invention is preferably endowed with a manipulation pocket intimately associated to the footplate. This association is made via the advantageous cooperation between the pocket and said tool tip, so that the tool by itself contributes to the invention.

In particular, it is provided such a tool comprising:
 a handle;
 a straight rod comprising a first extremity fixed to the handle;
 a circularly curved rod that smoothly extends from a second extremity of the straight rod;
 a tip fixed to the circularly curved rod,
 secantly extending from the circularly curved rod, and
 dimensioned for cooperating with the pocket by a (keyed) engagement of the tip into the pocket, so that a moving of the elongated flexible footplate can be induced by a moving of the tool.

The tool allow to implant the IOL according to the invention easily. In particular, this only tool is sufficient for performing all the necessary steps of the implantation process. In addition, during the latter, it is not necessary to touch the footplate with the tool tip for positioning it. This advantageously prevents the surgeon from making a manipulation error such as engaging the tip into a cavity surrounded by the footplate with the risk to touch delicate intraocular tissues, e.g. the crystalline lens.

The tool design is specifically adapted to an easy implantation of the IOL in the eye posterior chamber. In particular, the circular curved rod and the tip are preferably the only parts of the tool penetrating into the eye. The circular curved rod allows to avoid potential sharp angle between the straight rod and the tip. It is in particular dimensioned for allowing the tip to reach smoothly the pocket through the posterior chamber without damaging intraocular tissues and without touching the IOL which could push the latter posteriorly, undesirably deform it, and/or touch the crystalline lens, leading so to a cataract of the eye. The circularly curved rod preferably substantially extends along a single arc of circle with a radius of curvature more preferably comprised between 10 and 30 mm, e.g. of about 20 mm. The circularly curved rod may nevertheless comprise a plurality of circularly curved parts, preferably two such parts, with different radii of curvature in the framework of the invention. For two circularly curved parts (connected), the first radius of curvature (of the first part) is preferably comprised between 10 and 30 mm, e.g. of about 20 mm, and the second radius of curvature (of the second part) is preferably comprised between 5 and 10 mm, e.g. of about 6 mm. In an advantageous way, the second part has a steeper inclination pointing downward which makes the more adapted to reach the pocket without touching the IOL with another part of the tool. More generally and more preferably, when the circularly curved rod comprises a plurality of circularly curved parts, their respective radii of curvature are decreasing from the straight rod to the tip for a similar reason.

The tip is typically the only part of the tool arranged for cooperating and engaging into the pocket. Preferably, it comprises a free extremal (or distal) portion with a sharp ending edge configured for hooking the tip into the pocket. This external portion is preferably cylindrically shaped. In particular, the design of the tool tip is then very simple and the tool is easy to manufacture although allowing for an efficient keyed engagement into the pocket.

For a pocket corresponding to a trench on IOL anterior surface, the trench width is typically exactly dimensioned for receiving the tip, so that the tip engages in the trench and has substantially one free degree of movement along the extension trajectory of the trench. The latter may have in particular a similar shape as the footplate. In particular, the external portion is typically arranged for engaging axially into the pocket, and then to move into the pocket, on the IOL anterior surface.

Preferably, the tip comprises a bulged portion fixed (or connected) to the circularly curved rod. This bulged portion allows to extend quite smoothly the circularly curved rod, and to define a smooth angle between the circularly curved rod and an axis of extension of the external portion of the tip (which is preferably parallel to the optical axis when the tool is in use). The term "bulged" is used to refer to the form of this portion, the latter being more preferably at least partially ellipsoidal. The cross sections of the bulged portion are preferably larger (e.g. in terms of diameter and/or area) than the constant cross section of the extremal portion, in such a way that only the extremal portion may engage into the pocket. In particular, and very advantageously, the bulged portion acts as a stopper for preventing the tool to enter into any IOL hole or cavity. The cross sections of the bulged portion are typically elliptical (e.g. circular). A first elliptical section of the bulged portion is preferably at least 25% larger, more preferably at least 50%, more preferably again at least twice larger, than a second constant circular section of the extremal portion.

The extremal portion is preferably directly and sharply fixed on the bulged portion in such a way that the tip may hook more easily on the IOL anterior surface at the level of the pocket. Alternatively, the extremal portion is smoothly fixed to the bulged portion by use of an intermediate mechanical connection. This mechanical connection has typically a smoothly variable cross section geometry which may prevent undesirable hooking of the budge portion on the IOL during the implantation process.

Preferably, the bulged portion comprises a curved subportion oriented for mimicking the peripheral haptic part anterior curvature when the tip external portion extend axially. This subportion provides the tool with a global form again more adapted for allowing the extremal portion to reach the pocket without touching the IOL with another part of the tool.

The straight rod, the circularly curved rod and the tip of the tool are preferably made of metal, e.g. of stainless steel, which makes it resistant.

The invention also provides a set comprising the IOL according to the invention and the above introduced tool. All the embodiments of the IOL and/or of the tool mentioned above, as well as their mutual advantages extend mutatis mutandis to the present set.

BRIEF DESCRIPTION OF THE FIGURES

Other features and advantages of the present invention will appear on reading the detailed descript that follows, for the understanding of which, it is referred to the attached drawings.

The list of these drawings is the following.

Figure 1:
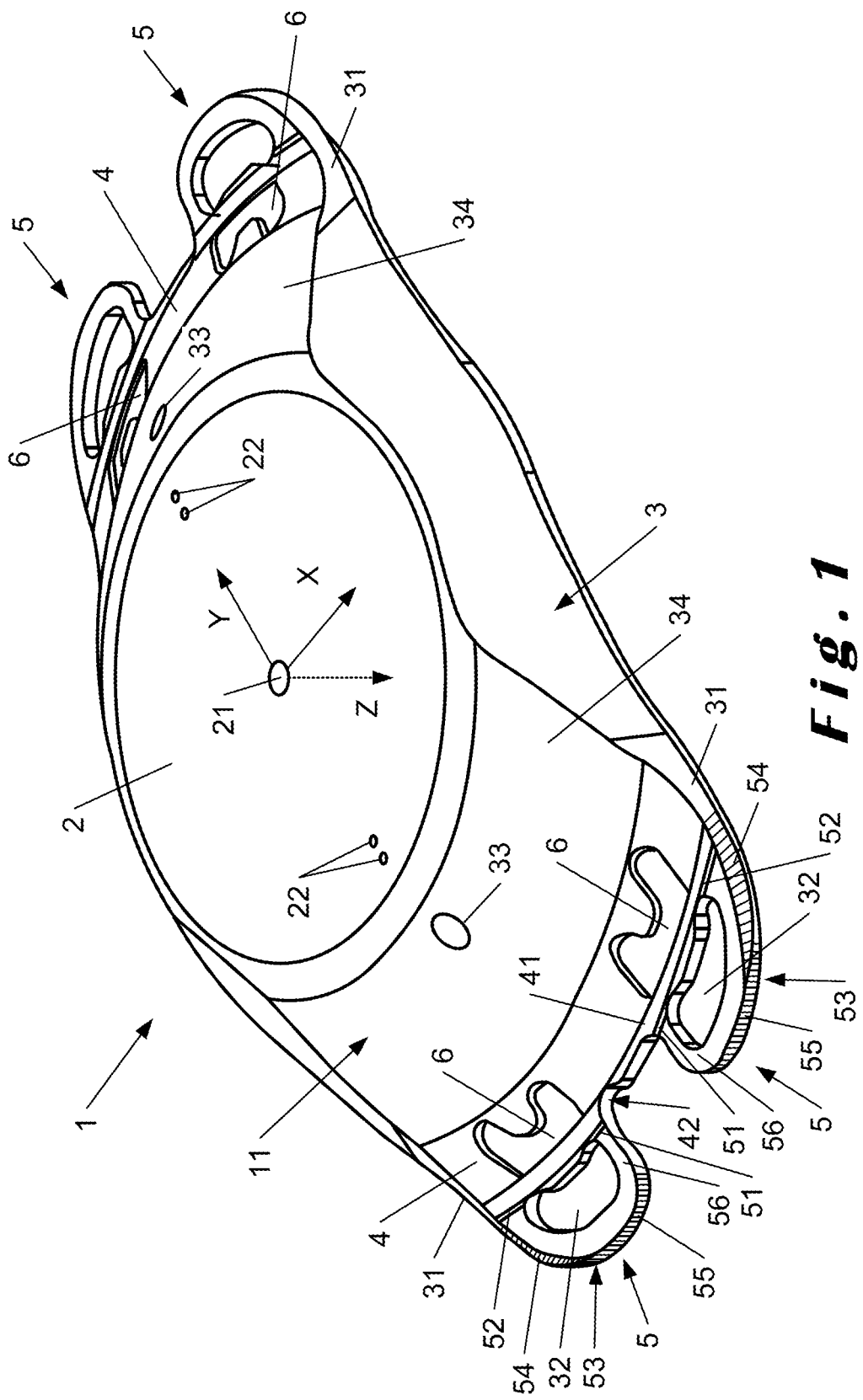
FIG. 1 illustrates a global tridimensional anterior and lateral view of an IOL according a preferred embodiment of the invention.

The drawings are typically not scaled. Similar elements are generally assigned by similar references. In the framework of this document, identical or analogous elements may have the same references. Moreover, the presence of reference in the drawings cannot be considered to be limiting, comprising when these references are indicated in the claims.

Detailed Description of Specific Embodiments of the Invention

This part of this document presents a full description of specific and preferred embodiments of the present invention with references to the drawings. The invention is however not limited by these references. The Figures that were introduced above are in particular only schematic and not limiting in any way.

Some of the Figures are provided with abstract geometric marks and corresponding references (e.g. 81 to 89B, X, Y, Z, K, P, k, k', 7A, 7B, 71A, 72A, 72B, 73A, $\alpha$ to $\varepsilon$, and $\theta$) substantially used to quantify and/or visualize technical characteristics of embodiments of the invention such as measures or geometric characteristics. These geometric marks generally do not correspond to concrete material objects.

The invention provides a posterior chamber phakic IOL 1 that is at the same time adapted to a broad range of eye anatomies, easy to implant and postoperatively stable in an implantation position in an eye 9, axially along an optical axis Z, radially and in rotation in a plane perpendicular to the optical axis Z based on vectors (or axis) X and Y. In particular, as illustrated in FIG. 1, the axis X, Y and Z form an orthogonal basis of the Euclidian tridimensional space. As conventionally, the optical axis Z is directed from an anterior surface 11 to a posterior surface 12 (referenced on FIGS. 1 and 3) of the IOL 1.

Figure 5:
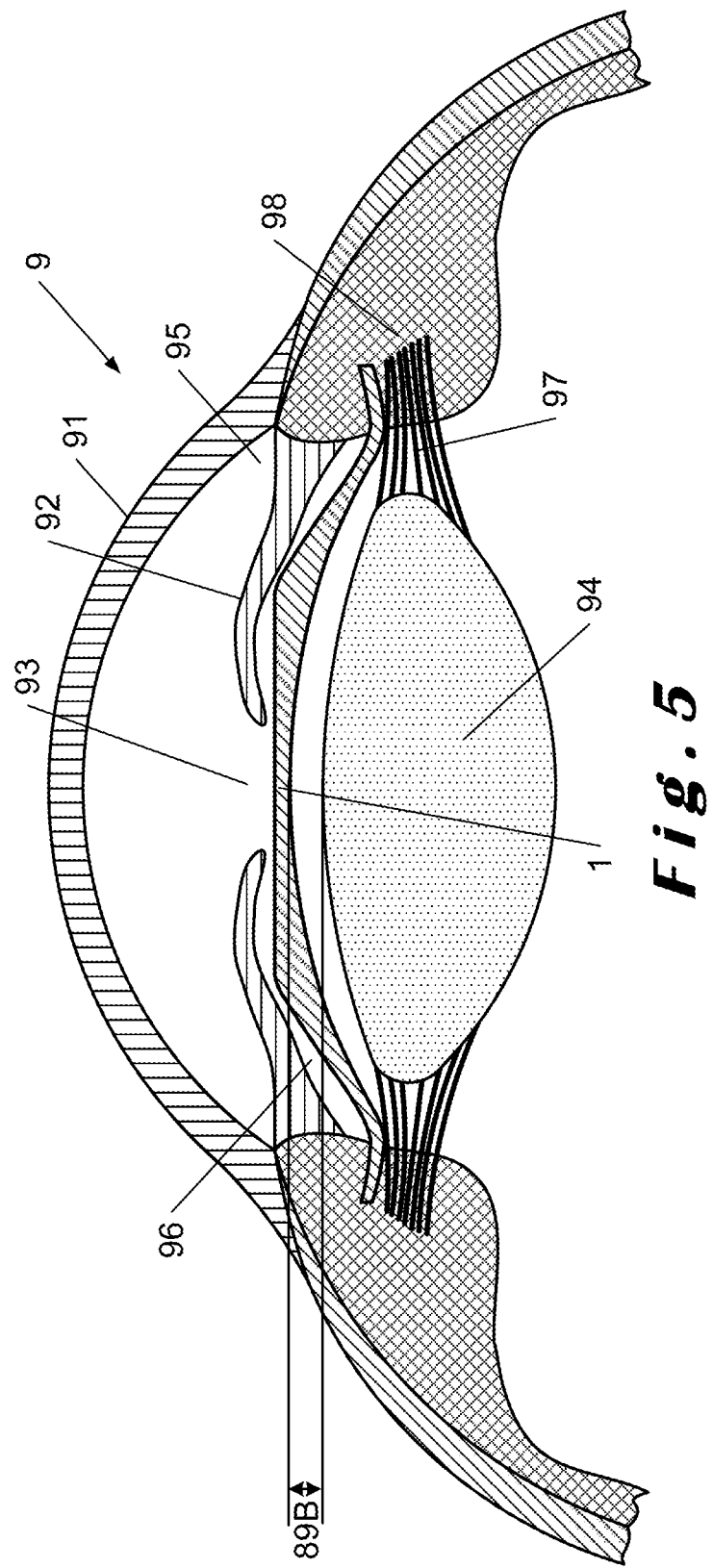
FIG. 5 illustrates a sectional view of part of an eye wherein is fitted the IOL illustrated in FIG. 1, the latter being illustrated by a side shadow view.

As represented on FIG. 5, the IOL 1 is intended to be positioned in the posterior chamber 96 of an eye 9. Other elements of the eye 9 anatomy are illustrated on FIG. 5: a cornea 91, an iris 92, a pupil 93, a crystalline lens 94, an anterior chamber 95, a ciliary zonule 97 and a ciliary body 98 of the eye 9.

Figure 2:
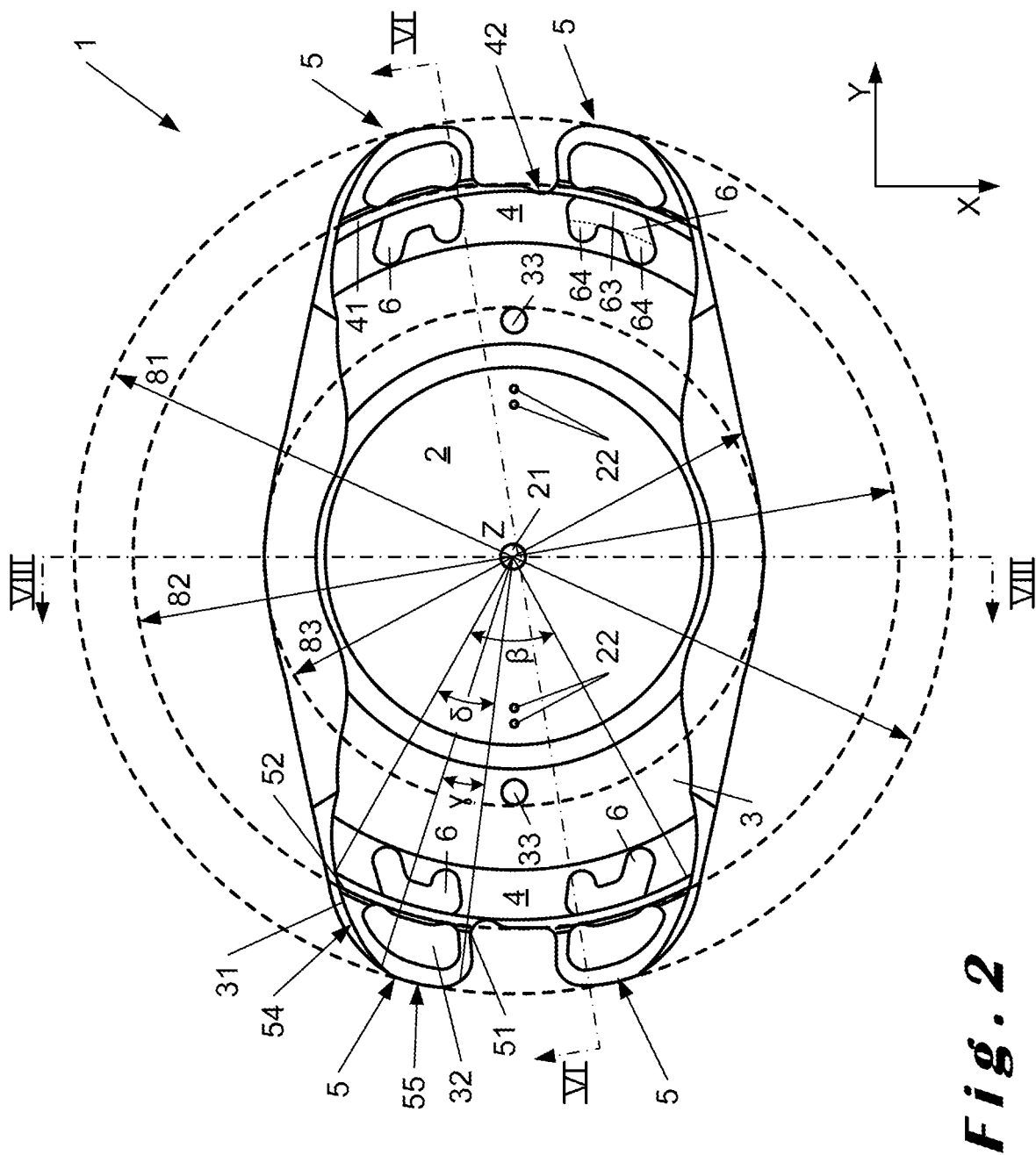
FIG. 2 illustrates a planar top view of the IOL illustrated in FIG. 1.

As illustrated in FIGS. 1 and 2, the IOL 1 has a central optical part 2 extending radially relative to the optical axis Z on a maximal external diameter comprised between 4.5 and 6.7 mm, preferably of about 5.8 mm. It comprises a through bore 21 extending along the optical axis Z between the anterior 11 and posterior 12 surfaces, so that a fluid communication is possible between these surfaces. The central optical part 2 also comprises orientation marks 22 in form of two pair of diametrically opposed tiny superficial holes aligned along axis Y on the anterior surface 11. Those marks 22 can be used for orienting the IOL 1 during its implantation. Exemplary diameters values of the through bore 21 and each superficial hole are respectively about 0.36 and 0.12 mm.

The central optical part 2 is surrounded by haptic structures among which a peripheral haptic part 3 circumferentially and proximally mounted on the central optical part 2. The peripheral haptic part 3 extends radially outward and posteriorly relative to the central optical part 2. It extends nevertheless further radially along axis Y than along axis X, so that the IOL has a global planar form elongated along axis Y as illustrated on FIG. 2.

The peripheral haptic part 3 is composed of a main proximal portion 34 and two diametrically opposed distal support elements 4. The main proximal portion 34 comprises two peri-optical holes 33 arranged proximally close to the boundary with central optical part 2, along axis Y, symmetrically with respect to the optical axis Z. The peri-optical holes 33 cross the IOL 1 through the anterior 11 and the posterior 12 surfaces so that they allow a fluid flow during the IOL 1 implantation process. As represented on FIG. 2, the peri-optical holes 33 are comprised in a IOL 1 part of a third diameter 83 comprised between 7.2 to 8.0 mm, preferably of about 7.45 mm. The peri-optical holes 33 are preferably quite similar to the through bore 21 in terms of size.

The support elements 4 are attached on two diametrically opposed distal extremities of main proximal portion 34, in mirror symmetry with respect to a plane based on axis X and on the optical axis Z. They have the form of a ring portion extending circumferentially around the optical axis Z, each along an arc of circle with a central angle β of about 60° (visible on FIG. 2). A distal border 41 of each support element 4 extends in particular along an arc of circle of a second diameter 82 comprised between 9.5 and 11.1 mm, e.g. of about 10.4 mm. It comprises a lateral recess 42 in the form a partial hole increasing the distal border 41 flexibility.

In particular, the whole peripheral haptic part 3 and the central optical part 2 are inscribed in a cylinder of the second diameter 82 extending around the optical axis Z, in such a way to form a dome K (or dome assembly) that is supported posteriorly by the support elements 4. As shown on FIGS. 3 and 5, the dome K has a posterior surface intended to top a crystalline lens 94 when the IOL 1 is in its implantation position in an eye 9. The distal support elements 4 are then arranged for supporting the IOL 1 on a ciliary zonule 97 of the eye 9.

The dome K posterior surface is concave, smooth, and curved with a preferred radius k of curvature of about 10 mm compatible with the curvature of the crystalline lens 94 anterior surface, so that a vault 89B adjustable between 300 and 750 μm can be ensured between the IOL 1 and the crystalline lens 94 when the IOL 1 is in its implantation position as explained in the disclosure of the invention and shown on FIG. 5.

Figure 3:
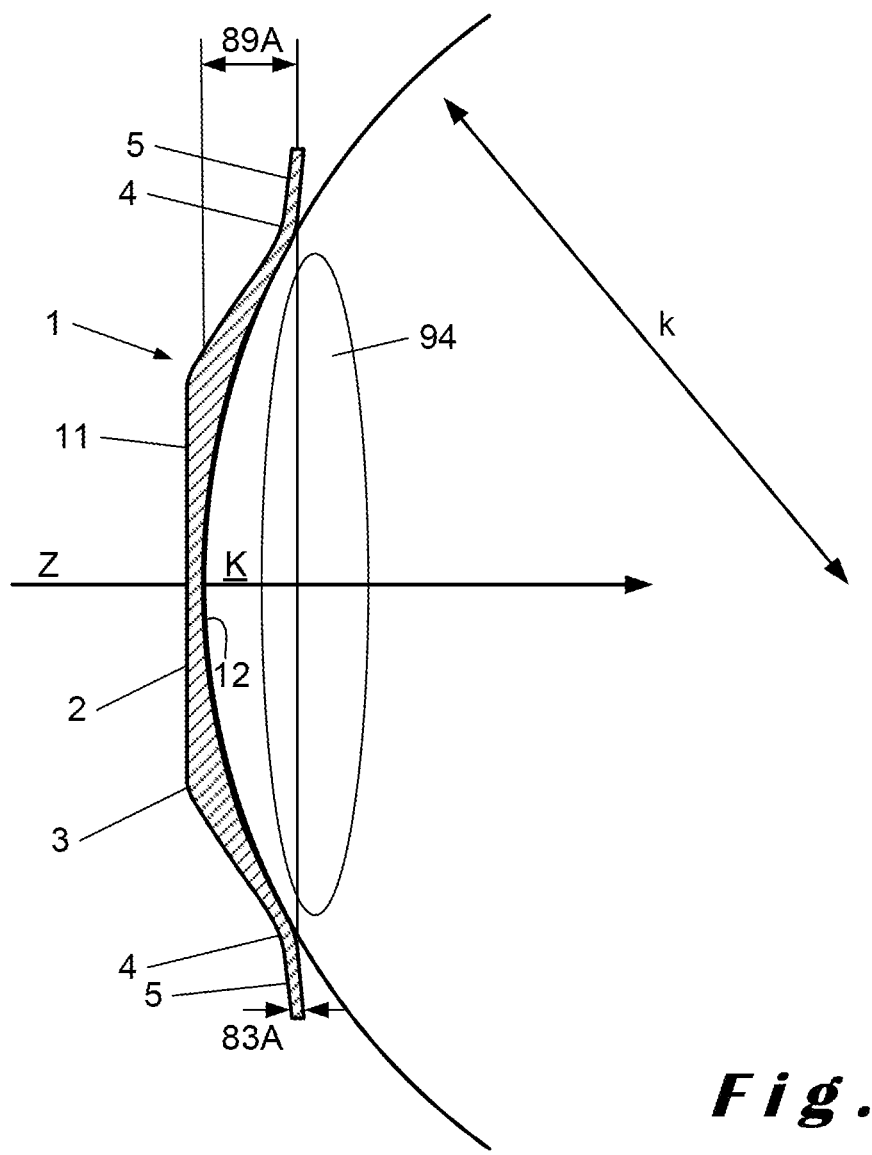
FIG. 3 illustrates a side shadow view of the IOL illustrated in FIG. 1 with a relative positioning of an IOL induced dome and an eye crystalline lens.

A inherent height 89A of the dome K visible on FIG. 3, measured axially, said "inherent vault", constitutes a height of a vault inherent to the IOL 1. It has a value typically comprised between 1.0 and 2.0 mm, preferably between 1.3 and 1.75 mm. For instance, if the pair composed of a first diameter 81 of the IOL 1 and said second diameter 82 is (12.7 mm, 9.5 mm), (13.2 mm, 10.4 mm) or (13.6 mm, 11.1 mm), then the inherent height 89A is about 1.30, 1.40 or 1.75 mm respectively.

Figure 8:
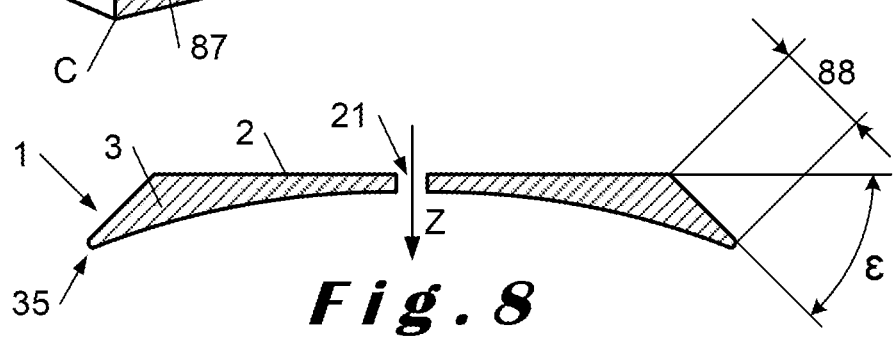
FIG. 8 illustrates a sectional view of the IOL illustrated in FIG. 1 along the plane VIII represented on FIG. 2.

As shown on FIG. 8, the lateral sides of the peripheral haptic part 3 on which no support element 4 is distally mounted comprise slope with an angle ε of about −45° with respect to a plane perpendicular to the optical axis Z. The slope has a length 88 comprised between 0.8 and 1.3 mm, preferably of about 1.06 mm. It ended with a distal rounded polished corner 35 oriented posteriorly and radially.

As explained in the disclosure of the present invention, a certain wall thickness confers rigidity to the dome K so that it is resistant under axial and/or radial compression when the IOL 1 is in its implantation position. In particular, as represented on FIG. 6, a thickness 84C of the dome K around its center may be about 0.20 mm, then it increases radially till reaching the proximal boundary of the peripheral haptic part 3, having for instance a thickness 84 B of about 0.60 mm, and finally decreases radially till the support elements 4 having a thickness 84A generally comprised between 0.15 to 0.25 mm (without taking into account the pockets introduced hereafter).

These values are selected so that the dome K is able to constitute a sufficiently rigid and broad structure to surround and top anteriorly a crystalline lens 94, and thereby to be implanted in a broad range of eye anatomies, while being stable in parallel to the optical axis Z.

Figure 7:
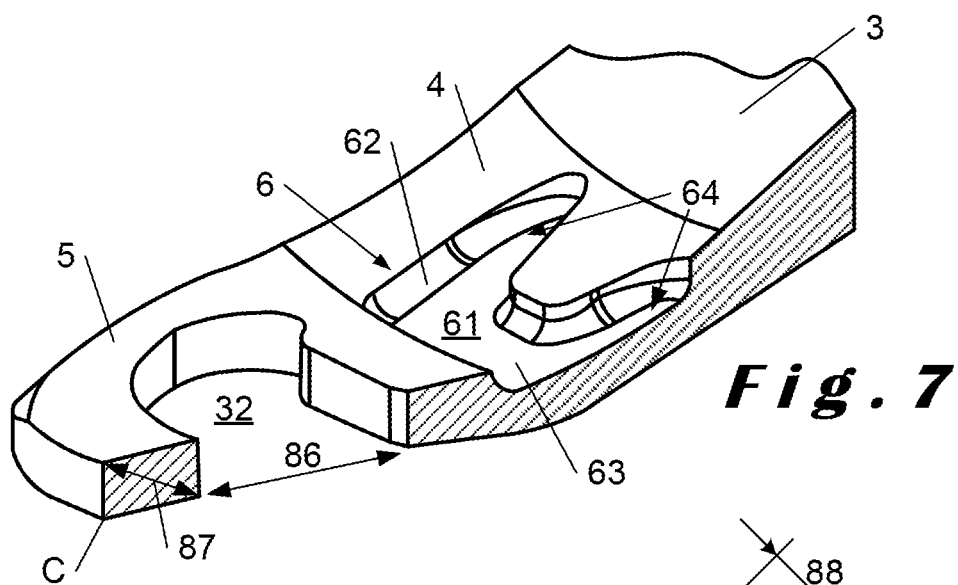
FIG. 7 illustrates a tridimensional enlarged view of a section of a support element and a footplate of the IOL illustrated in FIG. 1.

As illustrated clearly in FIGS. 1, 2 and 7, the IOL 1 also comprises two pair of diametrically opposed elongated flexible footplates 5 mounted on the distal support elements 4, extending radially along axis Y beyond the peripheral haptic part 3. Each such footplate 5 has a first 51 and second 52 extremities mounted on the same support element 4, so that the footplate has a form of a partial loop bordering a cavity 32 extending from the anterior 11 to the posterior 12 surfaces.

The first extremity 51 is arranged centrally along the distal border 41, while the second extremity 52 is arranged laterally along the distal border, in the continuation of a lateral side of the peripheral haptic part 3. In other words, the first extremity 51 is closer to axis Y than the second extremity 52. As shown on FIG. 2, the distal border 41 extends between the first 51 and the second 52 extremities along a circular arc of the second diameter 82 with a central angle δ comprised between 15° and 45°, preferably of about 20° to 25°.

Each cavity 32 is more extended in terms of area perpendicularly to the optical axis Z than the corresponding footplate 5. In particular, as shown on FIG. 7, a maximal radial length 86 of each cavity 32 is (much) greater than a maximal diameter 87 of any cross section C of the elongated flexible footplate. This radial length 86 is comprised between 0.7 and 0.9 mm, preferably of about 0.8 mm, and the radial length of said cross section C is preferably comprised between 0.2 and 0.4 mm. As a consequence, the surface of the IOL 1 extending radially further than the second diameter 82 is emptier of a solid matter that full of a solid matter. Each footplate 5 has substantially a constant thickness 83A (shown on FIG. 3) comprised between 0.10 and 0.20 mm, preferably of about 0.15 mm. All these data contributes to give a great flexibility to the footplate 5.

The IOL 1 is globally inscribed in a cylinder of said first diameter 81 with a preferred value comprised between 12.7 and 13.6 mm prior to implantation, when no axial or radial compression is exerted on the IOL 1. In particular, each footplate extends between the second 82 and the first 81 diameters, so that its flexibility allows to compensate size variations of an anatomical space available in the eye posterior chamber 96 for the IOL 1 when the latter is in its implantation position as explained above in the disclosure of the invention.

Figure 6:
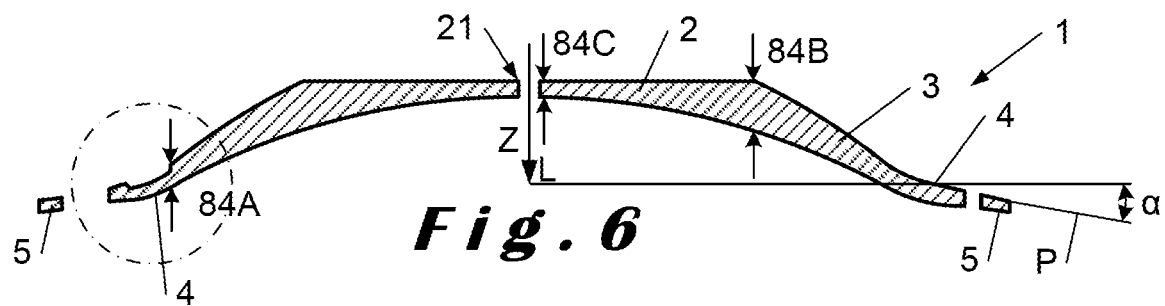
FIG. 6 illustrates a sectional view of the IOL illustrated in FIG. 1 along the plane VI represented on FIG. 2.
Figure 6A:
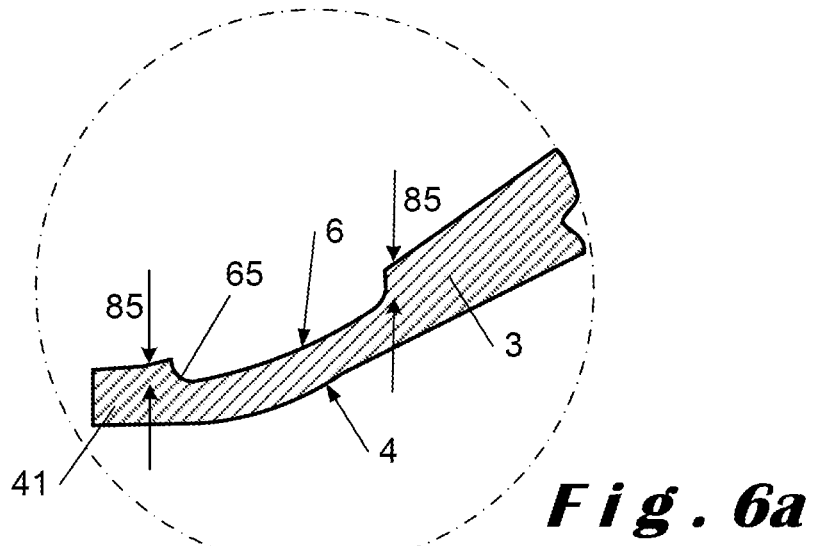
FIG. 6a illustrates an enlargement view of the encircled part of FIG. 6.

The footplate 5 is in particular designed for folding and/or for curving when compression is exerted axially and/or radially on IOL 1, in such a way that an adjustable angle α between the optical axis Z and a normal vector to a plane P of extension of the footplate 5 is generally comprised between −15° and 15°, as illustrated in FIG. 6.

Each footplate 5 comprises a distal lateral border 53 extending both circumferentially and radially outward relative to the support element 4 on which it is mounted. This distal lateral border 53 is in particular arranged for stabilizing the IOL 1 into the ciliary body 98 when the IOL 1 is in its implantation position as illustrated on FIG. 5. It acts as an anchor for stabilizing the IOL 1 in rotation in a plane perpendicular to the optical axis Z as detailed in the disclosure of the invention. The distal lateral border 53 may optionally be arranged for stabilizing the IOL 1 into the ciliary sulcus of the eye 9, so that the terms "ciliary body" in the present document could optionally be replaced by "ciliary body and/or sulcus".

Figure 4:
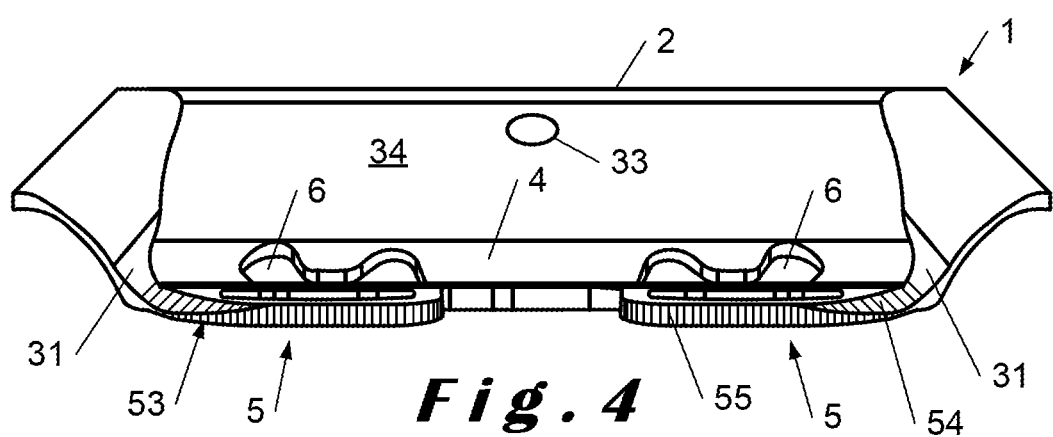
FIG. 4 illustrates a tridimensional strictly lateral view of the IOL illustrated in FIG. 1.

The distal lateral border 53 is composed of a first 54 and a second 55 portions particularly visible on FIGS. 1 and 4. As represented on FIG. 2, the second portion 55 extends along a circular arc of the first diameter 81 with a central angle γ comprised between 7.5° to 20°, and typically of about 10° when no axial or radial compression is exerted on the IOL 1. It consists therefore in the most distal part of the distal lateral border 53. The first portion 54, for its part, extends from the second extremity 52 to the second portion 55.

The first portion 54 is advantageously endowed with a smooth lateral chamfer 31. The latter extends laterally, smoothly and continuously on the first portion 54, on the support element at which is attached the second extremity 52 and on all or part of the main proximal portion 34 of the peripheral haptic part 3. As detailed in the disclosure of the invention, this chamfer 31 contributes to help to insert the footplate 5 under an iris 92 during the implantation of the IOL 1.

The footplate 5 itself consists substantially in three portions: a natural first width extension of the first portion 54, a natural second width extension of the second portion 55, and a third portion 56 visible on FIG. 1 connecting the natural second width extension and the first extremity 51. The main extension trajectory of these footplate portions extends respectively both circumferentially and radially, substantially only circumferentially and substantially only radially in a direction having a smaller angle with axis Y (corresponding typically to (½)(β−2δ)) comprised between 5 and 60°, e.g. of about 7.5° in the case of the illustrated embodiment of the invention. This angle allow advantageously to decrease the exerted compression forces on the IOL 1 when it is in its implantation position. In particular, an higher angle than 7.5°, such as 10°, 12.5°, 15°, 17.5°, 20°, 25°, 30° or 40° is also preferred as the greater it is, the lower are the exerted compression forces on the IOL 1.

The global design of the elongated flexible footplates 5 is determined to facilitate the IOL 1 implantation process. In particular, the chamfer 31 has a concave smooth external surface so that each footplate 5 is distally oriented in a convergent way toward the axis Y. Movements to insert the elongated flexible footplates 5 under the iris 92 are then greatly easier. The distal border 41 of each distal support element 4 extends further between the first extremities 51 of elongated flexible footplates 5 of two different pairs along a circular arc of the second diameter 82 with a central angle of about 15 to 20°.

Figure 9:
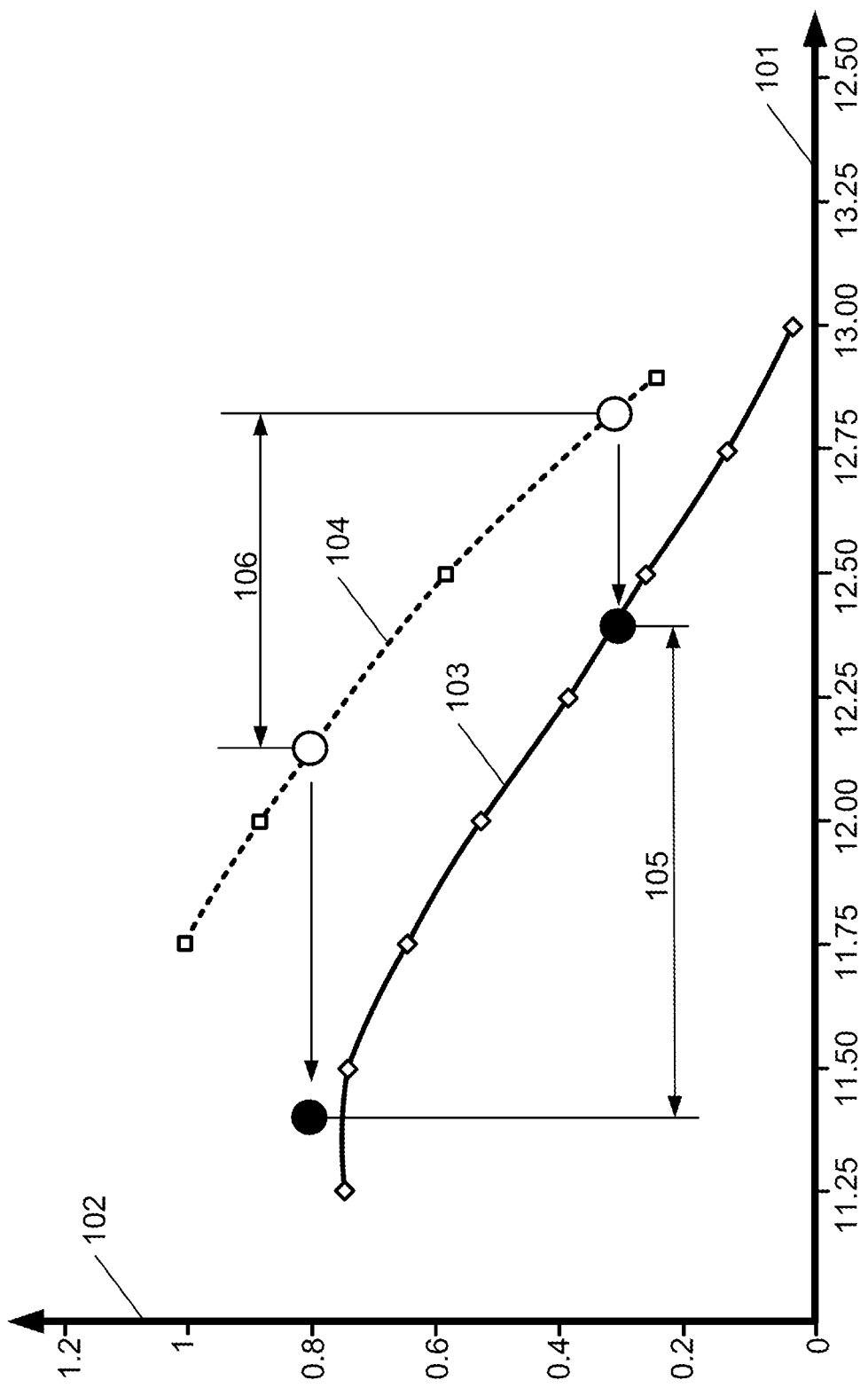
FIG. 9 illustrates a graphic representation of axial displacement of the IOL illustrated in FIG. 1 depending on a posterior chamber anatomical space.

The double haptic structure from the distal support elements 4 and the elongated flexible footplates 5 allows the IOL 1 to be particularly stable in its implantation position. A curve 103 in FIG. 9 represents the vault 89B (shown on FIG. 5), indicated on axis 102 and measured in mm, as a function of a size of a posterior chamber 96 anatomical space corresponding to a "ciliary body-to-ciliary body" measurement indicated on axis 101 and measured in mm, for an IOL 1 having a first diameter 81 value of 13.2 mm. The vault 89B values of 0.3 to 0.8 mm are considered as extremal for guarantying that the IOL 1 is axially stable and well positioned between the iris 92 and the crystalline lens 94. As visible on curve 103, this is the case for the IOL 1 with anatomical space size variations extending on about 1.1 mm (reference 105).

In comparison to curve 103, a similar curve 104 is drawn on FIG. 9 for known commercialized posterior chamber phakic IOLs with reduced massive distal footplates, and having then lower flexibility. As it can be seen on the curve 104, the adaptability of these IOLs to size variations of said anatomical space extend only on about 0.7 mm (reference 106), and is then significantly lower than 1.1 mm. The IOL 1 according to the invention is therefore able to cover a broader range of eye anatomies in a more stable way. This graphic comparison illustrates the performances and improvements in terms of axial stability of the invention.

Given that the elongated flexible footplates 5 are particularly flexible, it is advantageous to provide the IOL 1 with a structure for helping to control the elongated flexible footplates 5 movements during the implantation process and to insert them appropriately under the iris 92. To this end, the support elements 4 comprises manipulation pockets 6 on the IOL anterior surface 11 as it can be seen on FIGS. 1, 2, 6a and 7.

Each pocket 6 is associated with a footplate 5 in terms of structural and functional features. In particular, structurally speaking, each pocket 6 faces the associated footplate 5, so that only the distal border 41 separates the cavity 32 from the pocket 6. The pocket 6 is additionally radially aligned between the first 51 and second 52 extremities of the footplate 5. It defines a circumferential trench 63 on the IOL anterior surface 11 extending in parallel to the footplate 5 and comprising radially inwards extensions 64 arranged at two circumferential extremities of the trench 63, in mirror symmetries with the footplate extremities 51 and 52.

The trench 63 has a rough bottom surface 61 and lateral edges 62 of an axial height 85 of about 50% of the thickness 84A of the corresponding support elements 4. In other words, the axial height 85 is comprised between 0.075 and 0.125 mm, preferably between 0.08 and 0.09 mm. The height 85 may decrease slightly radially, depending on the support element 4 thickness 84A. The most distal lateral edge 65, at the boundary with the distal border 41, may be shaped in a half cylindrical form with radius 0.06 mm.

These geometrical features of the pockets 6 are especially provided in order to allow a functional cooperation with a tip 71 of a manipulation tool 7 by a geometrical keyed engagement of the tip 71 into the pocket 6, so that an appropriate moving of the elongated flexible footplate 5 during the implantation process of the IOL 1 can be induced by a moving of the tool 7.

Figure 11:
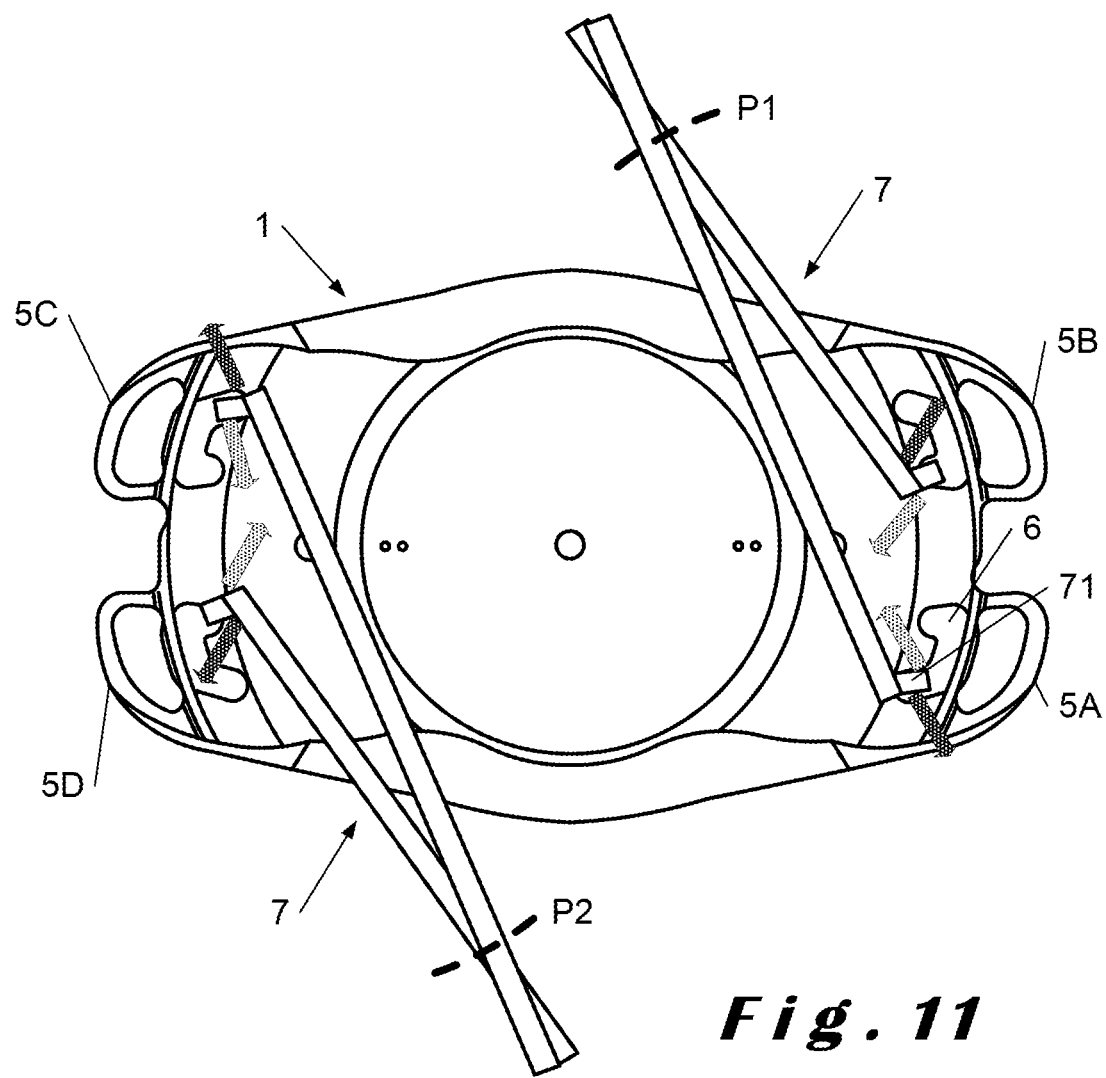
FIG. 11 illustrates a schematic top view of movements of the tip of the tool illustrated in FIG. 10 during the implantation process of the IOL illustrated in FIG. 1.

Such cooperation during the IOL 1 implantation process is illustrated schematically on FIG. 11. This Figure illustrated in particular movement of the tool 7 (by arrows) for inserting each of the footplate 5 under the iris 92 of a right eye 9. The elongated flexible footplates 5 are numbered from 5A to 5D in the order of their manipulation via the pocket 6.

The insertion process of the (right distal) footplate 5A comprises the following movements: pull towards a paracentesis (i.e. a small incision) P1, push down to insert the footplate 5A under the iris 92, push forward radially outwards. The insertion process of the (left distal) footplate 5B comprises the following movements: push towards a paracentesis P2, push down to insert the footplate 5B under the iris 92, pull radially outwards. For the (left proximal) footplate 5C, the insertion process comprises as movements: pull towards the paracentesis P2, push down to insert the footplate 5C under the iris 92, push forward radially outwards. Finally, concerning the (left distal) footplate 5D, the insertion process comprises the following movements: push towards the paracentesis P1, push down to insert the footplate 5D under the iris 92, pull radially outwards.

Figure 14:
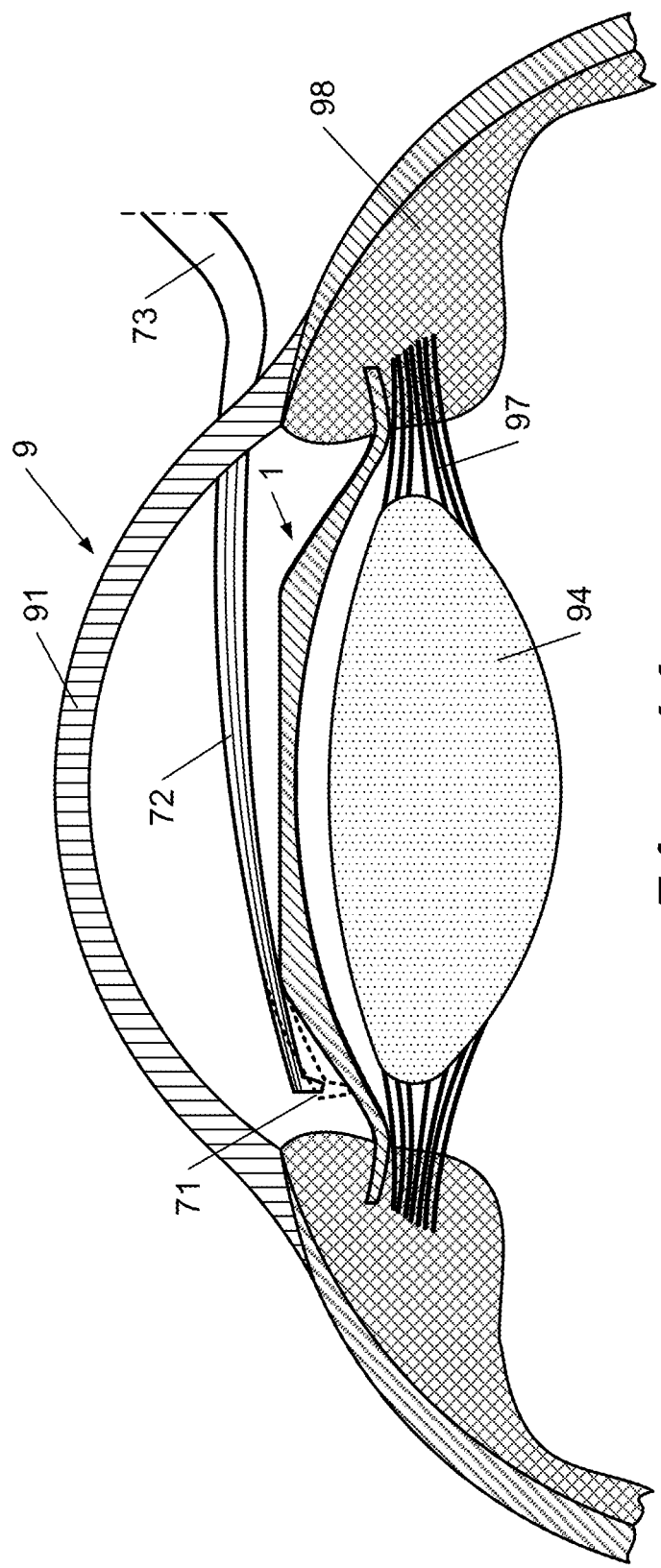
FIG. 14 illustrates a simplified sectional view of part of an eye crossed by part of the tool illustrated in FIG. 10 during the implantation process of the IOL illustrated in FIG. 1, the latter being illustrated by a side shadow view.

FIG. 14 illustrates the eye 9 of FIG. 5 during the implantation of the IOL 1. As it can be seen, the tip 71 of the tool 7 is specifically configured for cooperating with the pockets 6 and then allowing the above-mentioned insertion of the elongated flexible footplates 5A to 5D.

Figure 10:
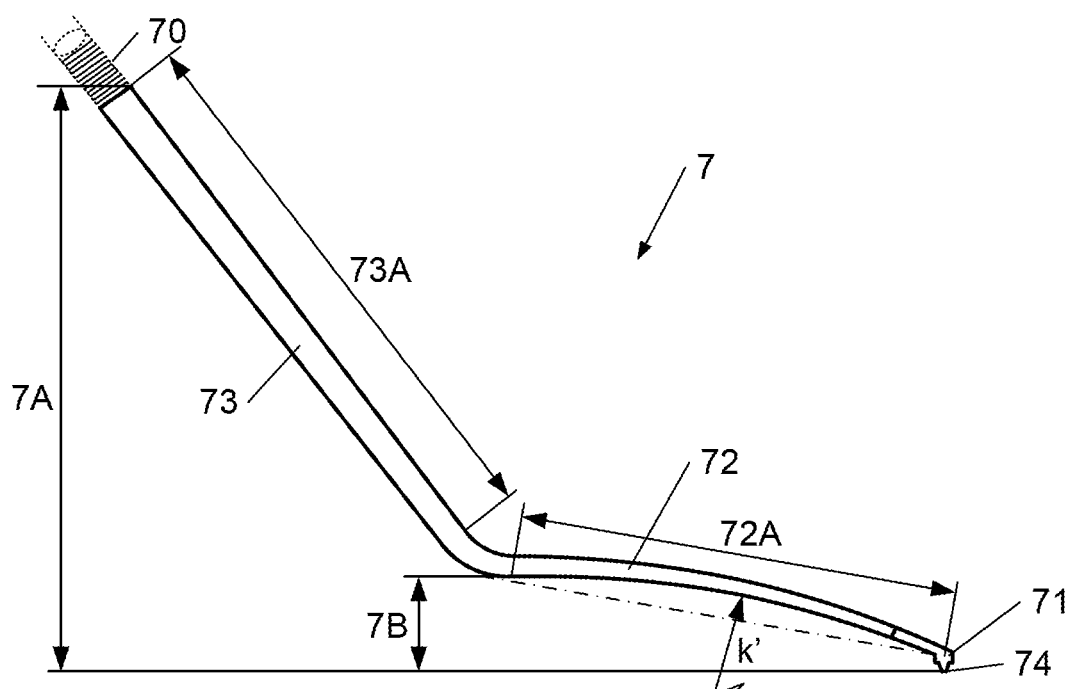
FIGS. 10 and 10A illustrate global planar side views of tools according preferred embodiments of the invention.
Figure 12:
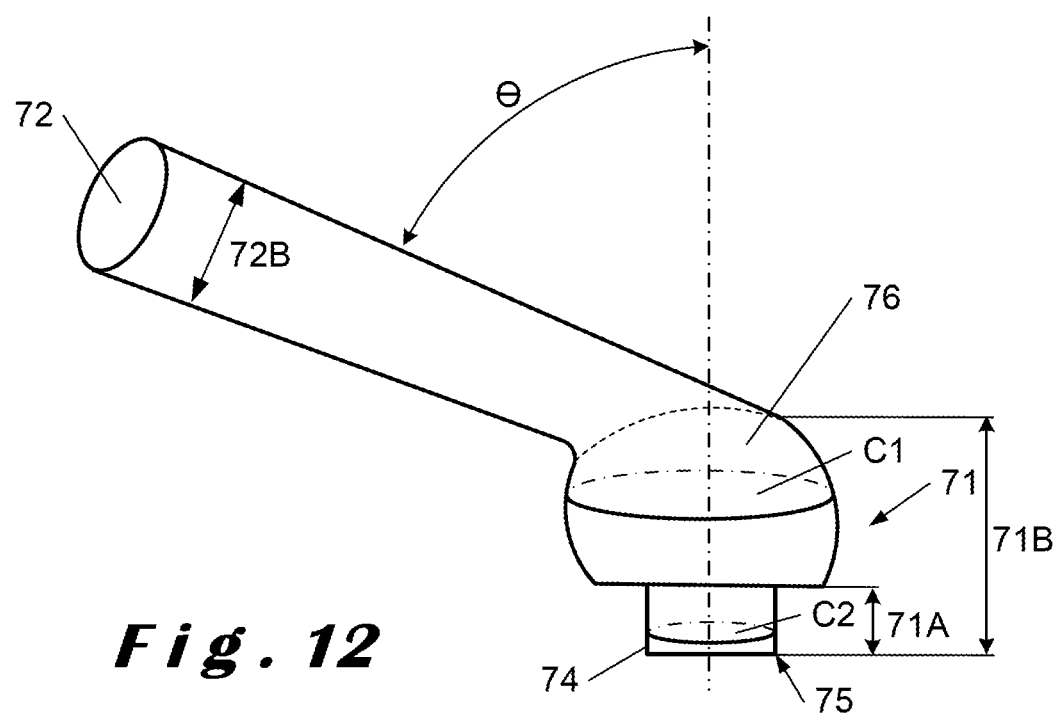
FIG. 12 illustrates a global tridimensional view of a first embodiment of the tip of the tool illustrated in FIG. 10.
Figure 13:
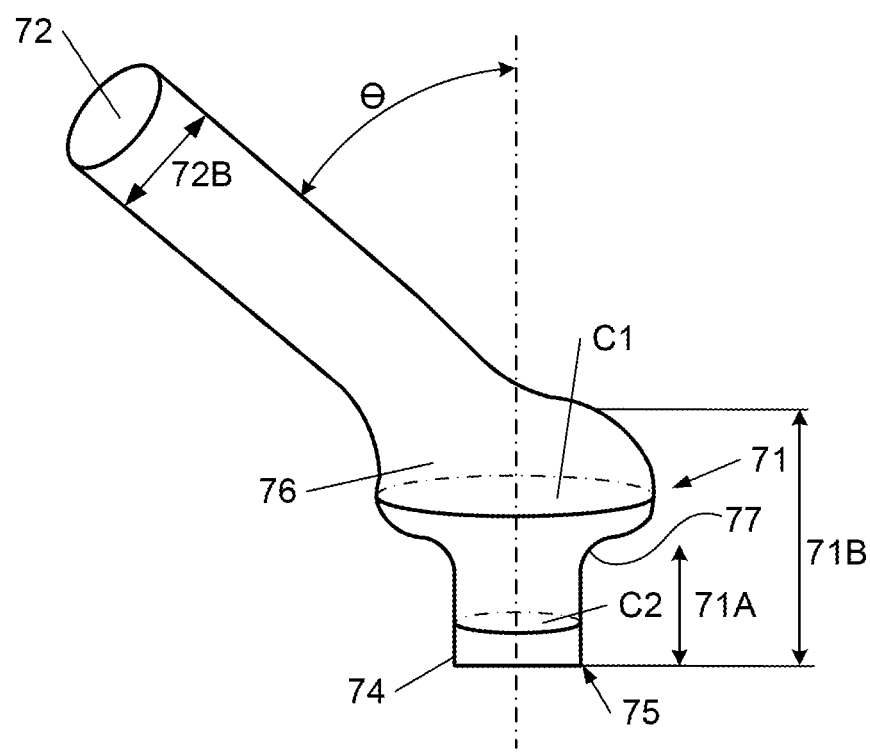
FIG. 13 illustrates a global tridimensional view of a second embodiment of the tip of the tool illustrated in FIG. 10.

The tool 7 is described in more details in view of FIGS. 10, 12 and 13. It comprises a handle 70, a straight rod 73 fixed to the handle, a circularly curved rod 72 smoothly fixed on the straight rod 73, and a tip 71 secantly fixed to the circularly curved rod 72. The tip 71 has a free (distal) extremal portion 74 cylindrically shaped arranged for engaging into the pocket 6.

It is provided non limitative exemplary dimensional values for the tool 7 when an inferior surface of the extremal portion 74 is in surface contact with the bottom surface 61, so that a revolution axis around which the free extremal portion 74 extends cylindrically is substantially parallel to the optical axis Z. In these conditions, as illustrated in FIG. 10, the tool 7 with the handle 70 has an axis length 7A of about 15.00 mm, the circularly curved rod 72 and the tip 71 has an axis length 7B of about 2.34 mm, the straight rod 73 extension length 73A is about 14.30 mm, the circularly curved rod 72 extension length 72A is about 11.30 mm and its radius of curvature k' is comprised between 15 and 30 mm, preferably of about 20, 21, 22, 23, 24, 25 or 26 mm. The width of the tool tends to decrease along the extension trajectory of the straight rod 73 and the circularly curved rod 72 from about 0.60 mm to about 0.24 mm at the neighborhood of the junction with the tip 71 (said latter width corresponding to the reference 72B on FIGS. 12 and 13). These values are chosen for allowing an appropriate orientation and position of the tool in the eye 9 as illustrated on FIG. 14.

Figure 10A:
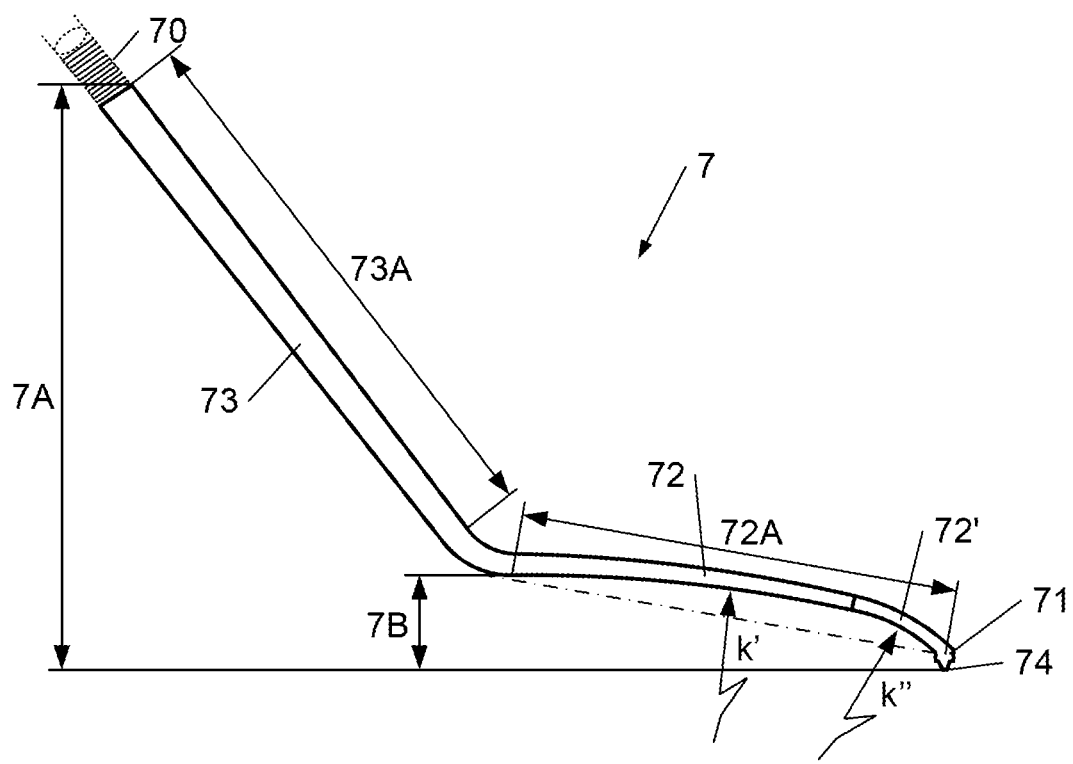

As described and shown on FIG. 10, the circularly curved rod 72 extends along a single arc of circle of the radius of curvature k'. Nevertheless, as shown on FIG. 10A, the circularly curved rod 72 may also comprises two parts with different radii of curvature. The second part 72' is more curved than the first part consisting in most of the circularly curved rod 72. In this case, the radius of curvature is preferably of about k', and the radius of curvature k'' of the second part is preferably of about 6 mm. Other features of the embodiment of FIG. 10 apply in FIG. 10A, e.g. the global length of the circularly curved rod 72. About 10 to 20% of this length originates from the second part 72'.

A different tip 71 may be provided on the tool 7, and may optionally be removable. Two embodiments of the tip 71 are illustrated on FIGS. 12 and 13. In both embodiments, the extremal portion 74 has an ending sharp edge 75 for hooking easily the tip 71 on the rough bottom surface 61 of the pocket 6. The cylindrical shape of the extremal portion 74 is particularly dimensioned for fitting with the pocket 6 size. It has a diameter of about 0.25 mm and is oriented with an smaller angle θ preferably comprised between 40° and 85°, e.g. it is of about 50°, 60°, 70° or 80°, and more preferably it is of about 51°, with respect to an extension direction of the circularly curved rod 72 in the neighborhood of its junction with the tip 71.

The tip 71 comprises a bulged portion 76 connecting the extremal portion 74 with the circularly curved rod 72. This connection through the bulged portion 76 may be made in different ways according to different embodiments among which two embodiments are illustrated in FIGS. 12 and 13. In each of the two embodiments, the bulged portion 76 has a first variable elliptical circular cross-section C1 larger than a second constant circular cross-section C2 of the free extremal portion 74, which allows to prevent the bulged portion 76 from entering into the pocket 6 and also to prevent the tip 71 from entering into an undesirable position, such as into the peri-optical holes 33 or the cavities 32.

The bulged portion 76 is fixed smoothly to the circularly curved rod 72 so that at least an axially top surface of the circularly curved rod 72 and the tip 71 is globally smooth. This allows advantageously to insert and to remove smoothly the tool 7 through small incisions (or said paracentesis P1 and P2), making then the above described insertion process and the tool 7 maneuverings easier.

On the embodiment of FIG. 12, the extremal portion 74 is directly and sharply fixed on a bulged portion 76 which improves the hooking of the tip 71 on the IOL 1 anterior surface, next to the pocket 6. On the embodiment of FIG. 13, the extremal portion 74 is differently smoothly fixed to the bulged portion 76 by an intermediate smooth mechanical connection 77.

The axial length 71A of the extremal portion 74 varies preferably from about 0.13 mm, e.g. for the embodiment of FIG. 12 to about 0.26 mm, e.g. for the embodiment of FIG. 13. The axial length 71B of the whole tip 71 is, for its part, preferably lower than 0.75 mm for both embodiments, and more preferably comprised between 0.45 and 0.60 mm, e.g. about 0.53 mm. This bounded axial length is in particular designed in order to allow for a smooth entering through small incisions (or said paracentesis P1 and P2) during the insertion process.

In other words, this invention relates to a posterior chamber phakic IOL 1 comprising a central optical part 2, a peripheral haptic part 3 having distal support elements 4 arranged for supporting the IOL 1 on a ciliary zonule 97 of an eye 9, elongated flexible footplates 5 mounted on the support elements 4, each having a distal lateral border 53 arranged for stabilizing the IOL 1 into a ciliary body 98 of the eye 9, and manipulation pockets 6 on a surface of the support elements 4, each pocket 6 being associated with one of the elongated flexible footplates 5.

The invention was described in relation to the specific embodiments which have a value that is purely illustrative and should not be considered to be limiting. Generally speaking, it will seem obvious for the person skilled in the art that the invention is not limited to the examples or measured values illustrated or described above. In particular, all the values mentioned in this description are provided with an error margin of 10%. The invention comprises each of the new characteristics described, as well as all their combinations.

The invention claimed is:

1. A posterior chamber phakic intraocular lens (IOL) comprising a central optical part surrounded by a peripheral haptic part from which extends an elongated flexible footplate, the peripheral haptic part comprising a manipulation pocket defining a blind hole adjacent to an extremity of the elongated flexible footplate and dimensioned for cooperating with a tip of a manipulation tool by a keyed engagement of the tip into the pocket so that a moving of the elongated flexible footplate can be induced by a moving of the tool.

2. The IOL according to claim 1, wherein the elongated flexible footplate has two extremities directly fixed to the peripheral haptic part so that the elongated flexible footplate forms a partial loop.

3. The IOL according to claim 2, wherein the pocket is radially aligned between said two extremities of the elongated flexible footplate.

4. The IOL according to claim 1, wherein the pocket defines a circumferential trench extending similarly as the elongated flexible footplate and dimensioned for receiving the tip of the tool along the trench.

5. The IOL according to claim 4, wherein a depth of the trench is comprised between 25 and 75% of a thickness of the peripheral haptic part at the pocket positioning.

6. The IOL according to claim 1, wherein the central optical part and the peripheral haptic part form a dome having a concave smooth posterior surface.

7. The IOL according to claim 1, comprising an anterior surface and a posterior surface, wherein the central optical part extends radially relative to an optical axis directed from the anterior surface to the posterior surface, wherein the peripheral haptic part is circumferentially mounted on the central optical part and extends radially outward and posteriorly relative to the central optical part, and wherein the manipulation pocket is arranged on the anterior surface and comprised in a distal support element of the peripherical haptic part, the support element being arranged for supporting the IOL on a ciliary zonule when the IOL is in an implantation position in an eye.

8. The IOL according to claim 7, wherein the support element is elongated along a circular arc with a central angle comprised between 2° and 80°.

9. The IOL according to claim 7, wherein the elongated flexible footplate borders a cavity extending from the anterior to the posterior surfaces, which is open along the optical axis and radially closed by the elongated flexible footplate, and wherein the cavity has a maximal radial length greater than any cross section of the elongated flexible footplate.

10. The IOL according to claim 7, wherein the elongated flexible footplate extends radially beyond the peripheral haptic part and comprises a distal lateral border extending circumferentially and radially outward relative to the central optical part and arranged for stabilizing the IOL into a ciliary body when the IOL is in the implantation position in the eye, and wherein the extremity of the elongated flexible footplate is directly fixed to said support element.

11. The IOL according to claim 10, wherein a smooth lateral chamfer extends smoothly and continuously from the support element to the distal lateral border.

12. The IOL according to claim 11, wherein the whole chamfer has a concave smooth external surface.

13. The IOL according to claim 10, wherein the IOL comprises two such diametrically opposed support elements, two pairs of diametrically opposed oriented elongated flexible footplates, each extending from one of the support elements and being associated with a manipulation pocket of this support element, and wherein the IOL is shape invariant under rotation of 180° around the optical axis.

14. The IOL according to claim 13, wherein the closest elongated flexible footplates from two different pairs are oriented in a convergent way toward a normal axis perpendicular to the optical axis, and spaced by a distance comprised between 5% and 25% of a peripheral haptic part external diameter measured along the normal axis.

15. A set comprising the IOL according to claim 1 and a manipulation tool, wherein the manipulation tool comprises:
a handle;
a straight rod comprising a first extremity fixed to the handle;
a circularly curved rod smoothly extending from a second extremity of the straight rod; and
a tip fixed to the circularly curved rod, secantly extending from the circularly curved rod, and dimensioned for cooperating with the pocket by a keyed engagement of the tip into the pocket, so that a moving of the elongated flexible footplate can be induced by a moving of the tool.

16. The set according to claim 15, wherein the tip has a free extremal portion cylindrically shaped with an ending sharp edge for hooking the tip into the pocket.

17. The set according to claim 16, wherein the tip comprises a bulged portion fixed to the circularly curved rod and having a first elliptical section at least 25% larger than a second constant circular section of the free extremal portion, and wherein the free extremal portion is either directly and sharply fixed on the bulged portion or smoothly fixed to the bulged portion by an intermediate mechanical connection.

18. The set according to claim 15, wherein the circularly curved rod comprises one or more of circularly curved parts with different radii of curvature.

19. A method of implantation of the IOL according to claim 1, comprising the step of maneuvering the elongated flexible footplate under the iris of an eye by moving a manipulation tool having a tip keyed engaged into the pocket.

20. The method according to claim 19, wherein the manipulation tool comprises:
a handle;
a straight rod comprising a first extremity fixed to the handle;

a circularly curved rod smoothly extending from a second extremity of the straight rod; and a tip fixed to the circularly curved rod, secantly extending from the circularly curved rod, and dimensioned for cooperating with the pocket by a keyed engagement of the tip into the pocket, so that a moving of the elongated flexible footplate can be induced by a moving of the tool.

* * * * *